US010641750B2

(12) United States Patent
Holba et al.

(10) Patent No.: US 10,641,750 B2
(45) Date of Patent: May 5, 2020

(54) PETROLEUM-FLUID PROPERTY PREDICTION FROM GAS CHROMATOGRAPHIC ANALYSIS OF ROCK EXTRACTS OR FLUID SAMPLES

(71) Applicant: CONOCOPHILLIPS COMPANY, Houston, TX (US)

(72) Inventors: Albert G. Holba, Houston, TX (US); Russell L. Bone, Houston, TX (US); Bradley J. Huizinga, Houston, TX (US); James R. Vasquez, Houston, TX (US); Sean M. Stokes, Houston, TX (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 13/957,911

(22) Filed: Aug. 2, 2013

(65) Prior Publication Data

US 2014/0208825 A1 Jul. 31, 2014

Related U.S. Application Data

(60) Provisional application No. 61/679,311, filed on Aug. 3, 2012.

(51) Int. Cl.
*G01N 30/88* (2006.01)
*G01N 33/28* (2006.01)
*G01N 30/86* (2006.01)

(52) U.S. Cl.
CPC ......... *G01N 30/88* (2013.01); *G01N 30/8682* (2013.01); *G01N 33/2823* (2013.01); *G01N 30/8651* (2013.01); *G01N 2030/8854* (2013.01)

(58) Field of Classification Search
CPC .................. G01N 33/2823; G01N 2030/8854
USPC ....................................................... 73/23.35
See application file for complete search history.

(56) References Cited

U.S. PATENT DOCUMENTS

| | | |
|---|---|---|
| 4,463,096 A | 7/1984 | Hughes |
| 5,866,814 A | 2/1999 | Jones et al. |
| 6,612,186 B1 | 9/2003 | Patten et al. |
| 6,823,298 B1 | 11/2004 | Jones et al. |
| 7,398,159 B2 | 7/2008 | Venkataramanan et al. |
| 7,805,979 B2 | 10/2010 | Reddy et al. |
| 7,920,970 B2 | 4/2011 | Zuo et al. |

(Continued)

OTHER PUBLICATIONS

Baskin and Jones, (1993) "Prediction of oil gravity prior to drill-stem testing in Monterey formation reservoirs, offshore California," AAPG Bulletin v, No. 9, p. 1479-1487.

(Continued)

*Primary Examiner* — Lisa M Caputo
*Assistant Examiner* — Alex T Devito
(74) *Attorney, Agent, or Firm* — Boulware & Valoir

(57) ABSTRACT

This method allows for prediction of subsurface fluid properties (e.g., phase or API gravity) using gas chromatogram data of a small-volume extract. Small volume equates to microliter scale volume (or milligram scale weight) from a subsurface rock sample, where a fluid test may not be available for analysis. The method may also be applied to petroleum liquid samples where drilling fluid or other contaminants preclude accurate direct property measurement. Gas chromatographic data is calibrated to measured petroleum properties; preferably local oils from the same petroleum system, however, a general global calibration can also be used.

16 Claims, 14 Drawing Sheets

(56) References Cited

U.S. PATENT DOCUMENTS

| | | |
|---|---|---|
| 2003/0195708 A1 | 10/2003 | Brown |
| 2004/0248307 A1 | 12/2004 | Grof et al. |
| 2007/0162264 A1 | 7/2007 | Jones et al. |
| 2008/0105032 A1 | 5/2008 | Reddy et al. |
| 2010/0089132 A1 | 4/2010 | Larter et al. |
| 2010/0095742 A1 | 4/2010 | Symington et al. |
| 2010/0271019 A1 | 10/2010 | Anand et al. |

OTHER PUBLICATIONS

Dennen, et al., "Pre-C02 Injection Reservoir Assessment, Naval Petroleum Reserve No. 3, Natrona County, Wyoming" U.S. Geological Survey Eastern Energy Resources Team (2007).
Dow, et al., "Determination of API Gravity from very small samples of oils, tar mats, and solid bitumens with Rock-Eval 6 Instrument." 18th Annual Meeting Abstracts and Program, The Society of Organic Petrology (TSOP), p. 41-42 (2001).
Dow and Talukdar, (1991) Petroleum geochemistry in oil production. 4th Assn. Colombiana Geol. Geofis. Petrol. Petrol. Explor. In the Sub-Andean Basins Bolivariana Symp. Bogata, (Colombia, Mar. 10-13, 1991) Memoir v. 2, No. 51.
Gabitto and Barrufet, "Experimental and theoretical determination of heavy oil viscosity under reservoir conditions," DOE Contract DE-FG26-99FT40615.
Holba, et al., "Effects and impact of early-stage anaerobic biodegradation on Kuparuk River Field, Alaska." In: Understanding Petroleum Reservoirs: Towards an Integrated Reservoir Engineering and Geochemical Approach. (eds.: Cubitt, J. M.; England, W. A.; and Larter, S.) Geological Society, London, special Publications 237, 53-88 (2004).
Hughes and Holba "Relationship between crude oil quality and biomarker patterns," Advances Organic Geochemistry 1987, Organic Geochemistry, 13, Nos. 1-3, 15-30 (1988).
Huizninga, et al., Heavy oils from the West Sak Field, North Slope Alaska: Geochemical oil property prediction and columnar gradients. (Abstract) AAPG Hedberg Conference: Heavy Oil and Bitumen in Foreland Basins—From Process to Products. Banff, Alberta, Canada, Sep. 30-Oct. 1, 2007.
Katz and Firoozabadi "Predicting phase behavior of condensate/crude-oil systems using methane interaction coefficients." SPE 6721, pp. 1649-1655 (1978).
Michael "Application of reservoir geochemistry to heavy oil, Venezuela." AAPG Annual Convention. May 11-14, (Abstract) (2003).
Smalley, et al., "New tools target oil quality sweetspots in viscous oil accumulations." SPE 36652 (1996).
Zhang, et al., Some exceptions to default NMR rock and fluid properties. 39th Annual SPWLA Logging Symposium (Keystone CO, May 26-29, 1998) Transactions (1998).
International Search Report dated Jan. 17, 2014.
Zeng et al., Gas Chromatograph Applications in Petroleum Hydrocarbon Fluids, Advanced Gas 1-19 Chromatography—Progress in Agricultural, Biomedical and Industrial Applications, Dr. Mustafa Ali Mohd (Ed.), ISBN: 978-953-51-0298-4, In Tech, Mar. 21, 2012.
Kissin, Y.V., et al., A Kinetic Method of Reactivity Ratio Measurement in Olefin Copolymerization With Ziegler-Natta Catalysts, Journal of Polymer Science: Polymer Chemistry Edition, vol. 21, 1065-1074 1983.
Chen, D.F., et. al., Seep Carbonates and Preserved Methane Oxidizing Archaea and Sulfate Reducing Bacteria Fossils Suggest Recent Gas Venting on the Seafloor in the Northeastern South China Sea, Marine and Petroleum Geology 22 (5), pp. 613-621 2005.
Chen, D.F., et. al., The Geochemical Signatures of Variable Gas Venting At Gas Hydrate Sites, Marine and Petroleum Geology, 21 (2004) 317-326.
Kissin, Y.V., Gas Chromatographic Analysis of Branched Olefins, Journal of Chromatographic Science 24 (7), pp. 278-284 1986.
Kissin, Y.V., Gas Chromatographic Analysis of Alkyl-Substituted Paraffins, Journal of Chromatographic Science 24 (2), pp. 53-59 1986.
Kissin, Y.V., Free Radical Cracking of High Molecular Weight Branched Alkanes, ACS Division of Fuel Chemistry, Preprints 30 (3), pp. 420-426 1985.
Kissin, Y.V., Free Radical Cracking of High Molecular Weight Branched Alkanes, American Chemical Society, Division of Petroleum Chemistry, Preprints 30 (4), pp. 652-657 1985.
Kissin, Yury V., et al., Dual-Functional Catalysis for Ethylene Polymerization to Branched Polyethylene. II Kinetics of Ethylene Polymerization With a Mixed Homogeneous—Heterogeneous Ziegler-Natta Catalyst System, Journal of Polymer Science, Part A: Polymer Chemistry 24 (6), pp. 1069-1084 1986.
Beach, D.L., et. al., Linear Dimerization of Propylene and 1-Butene Catalyzed by (H3—4-Cyclooctene-1-YL)-(1,1,1,5,5-HEXAFLUOR0-2,4-Pentanedionato)Nickel, Journal of Molecular Catalysis 34 (3), pp. 345-354 1986.
Revil, A., et. al., Fluid Transport by Solitary Waves Along Growing Faults a Field Example From the South Eugene Island Basin, Gulf of Mexico, Earth and Planetary Science Letters 202 (2), pp. 321-335 2002.
Losh, S., et al., Phase Fractionation and Oil-Condensate Mass Balance in the South Marsh Sland Block 208-239 Area, Offshore Louisiana, Marine and Petroleum Geology 27 (2), pp. 467-475 2010.
Losh, S., et al., Gas Washing of Oil Along a Regional Transect, Offshore Louisiana, Organic Geochemistry 33 (6), pp. 655-663 2002.
Losh, S., et al., Reservoir Fluids and Their Migration Into the South Eugene Island Block 330 Reservoirs, Offshore Louisiana, AAPG Bulletin 86 (8), pp. 1463-1488 2002.
Losh, S., et al., Massive Vein-Filling Gas Hydrate: Relation to Ongoing Gas Migration From the Deep Subsurface in the Gulf of Mexico, Marine and Petroleum Geology 18 (5), pp. 551-560 2001.
Whelan, J., et. al., Surface and Subsurface Manifestations of Gas Movement Through A N-S Transect of the Gulf of Mexico, Marine and Petroleum Geology 22 (4 SPEC. ISS.) pp. 479-497 2005.
Losh, S., et al., Vertical and Lateral Fluid Flow Related to a Large Growth Fault, South Eugene Island Block 330 Field, Offshore Louisiana, AAPG Bulletin 83 (2), pp. 244-276 1999.
Losh, S., Oil Migration in a Major Growth Fault: Structural Analysis of the Pathfinder Core, South Eugene Island Block 330, Offshore Louisiana, AAPG Bulletin 82 (9), pp. 1694-1710 1998.
Losh, S., Stable Isotope and Modeling Studies of Fluid-Rock Interaction Associated With the Snake Range and Mormon Peak Detachment Faults, Nevada, Bulletin of the Geological Society of America 109 (3), pp. 300-323 1997.
Losh, S., et al., The Impact of Pore Water Chemistry on Carbonate Surface Charge and Oil Wettability, Transport in Porous Media 85 (1), pp. 1-21 2010.
Cathles, L.M., et. al., The Physics of Gas Chimney and Pockmark Formation, With Implications for Assessment of Seafloor Hazards and Gas Sequestration, Marine and Petroleum Geology 27 (1), pp. 82-91 2010.
Su, Z., et. al., Numerical Computation and Case Analysis of the Venting Process of Free Gas Beneath Hydrate Layer, Chinese Journal of Geophysics (ACTA Geophysica Sinica) 52 (12), pp. 3124-3131 2009.
Cathles, L.M., The Potential Benefits to the Basin Modeling Enterprise of Modularization and Incorporating Organic and Inorganic Chemical Change, Marine and Petroleum Geology 26 (4), pp. 487-494 2009.
Chen, D.F., et. al., Types of Gas Hydrates in Marine Environments and Their Thermodynamic Characteristics, Terrestrial, Atmospheric and Oceanic Sciences 17 (4), pp. 723-737 2006.
Chen, D.F., et. al., On the Thermal Impact of Gas Venting and Hydrate Crystallization, Journal of Geophysical Research B: Solid Earth 110 (11), art No. B11204, pp. 1-13 2005.
Smalley, P.C., New Tools Target Oil-Quality Sweetspots in Viscous-Oil Accumulations, SPE Reservoir Engineering, pp. 157-161, Aug. 1997.
Tang, Y., Advanced Chemistry of Basin Modeling-Predicting Fluid Properties and Using Field Gas Isotope to Constrain Basin Modeling Uncertainty, AAPG International Conference (Rio de Janeiro, Brazil, Nov. 15-18, 2009) Abstract 2009.

(56) References Cited

OTHER PUBLICATIONS

Blumenstein, et al., Biodegradation in Numerical Basin Modelling: A Case Study From the Gifhorn Trough, N. Germany, International Journal of Earth Sciences, v. 97, No. 5, pp. 1115-1129, Sep. 2008.
Hashem, et al., Determination of Producible Hydrocarbon Type and Oil Quality in Wells Drilled With Synthetic Oil-Based Muds, Annu. SPE Tech. Conf. (San Antonio, Oct. 5-8, 1997) Proc. [Formation Evaluation and Reservoir Geogoly] pt.2, pp. 353-366, 1997. (SPE-39093).
Lamoureaux-Vara, et al., "Best Practice for Rock-Eval pyrolysis with emphasis on unconventional prospects," Analytic Techniques, Alago 2014.
Ikiensikimama & Ajienka, "Impact of PVT correlations development on hydrocarbon accounting: The case of the Niger Delta" Journal of Petroleum Science and Engineering, 81: 80-85 (2012) ISSN 0920-4105.
Moos, D., Fluid Detection and Porosity Determination Using Acoustic Logs in the Wilmington Field, CA, Annu. AAPG-SEPM-EMD-DPA-DEG Conv. (Dallas, Apr. 6-9, 1997) PAP. Abstr. pp. A84-A85, 1997 (Abstract Only).
Khavari Khorasani, G, et al., Gulf of Suez Petroleum System Charge: Volumes and Distribution of Light and Heavy Oil and the Controlling Factors, Annu. AAPG-SEPM-EMD-DPA-DEG Conv. (Dallas, Apr. 6-9, 1997) PAP. Abstr. p.A60, 1997. (Abstract only).
Elias, R., et al., Improved Assessment of Biodegradation Extent and Prediction of Petroleum Duality, Organic Geochemistry v. 38, No. 12, pp. 2111-2130 (2007) (ISSN 914505379).
Difoggio, R., Liquified-Gas Extraction and Near-Infrared Analysis of Core, 5th Annu. Soc. Core Anal. Tech. Conf. (San Antonio, Aug. 1991), Preprints v. 3, pap. No. SCA-9131, 1991.
Zuo, J.Y , et al , Modeling of Phase Equilibria and Viscosity of Heavy Oils, World Heavy Oil Congress (WHOC08), Edmonton, Alberta, Mar. 2008.
Al-Farhan, et al., Optimization of Surface Condensate Production From Natural Gases Using Artificial Intelligence, J. of Petroleum Science & Engineering v. 53, Nos. 1-2, pp. 135-147, Aug. 2006 (ISSN 0920-4105).
Tocco, R., et al., Organic Geochemistry of Heavy/Extra Heavy Oils From Sidewall Cores, Lower Lagunillas Member, Tia Juana Field, Maracaibo Basin, Venezuela, Fuel v. 81, No. 15, pp. 1971-1976, Oct. 2002 (ISSN 0016-2361).
Santamaria-Orozco, et al., Predicting Bulk Petroleum Compositions, AAPG Int. Conf. (Cancun, Mexico, Oct. 2004)(Available at http://www.aapg.org as of Jan. 25, 2006).
Bement, W.O., et al., Predicting Oil Quality From Sidewall Cores Using PFID, TEC [Pyrolysis Flame Ionization Detection, Thermal Extraction Chromatography], and NIR [Near Infra-Red Spectroscopy] Analytical Techniques in Sandstone Reservoirs, Rio Del Rey, Cameroon , Annu. AAPG-SEPM-EMD-DPA-DEG Conf. (Houston, Mar. 1995) Pap. Abstr.
Peters, K.E., Predicting Physicochemical Properties of Upper Jurassic Circum-Arctic Crude Oil, Annual AAPG Convention (Long Beach, CA, Mar. 2007) Technical Program (Available at http://www.aapg.org as of Jan. 2, 2007; 1 p; Abstract only).
Ferrer, J. (Jan. 1, 1977). A Three-Phase, Two-Dimensional Compositional Thermal Simulator for Steam Injection Processes. Petroleum Society of Canada. doi:10.2118/77-01-07.
Bergman, D.F., et al., Pseudo-Compositional Model for the Calculation of Liquid Viscosity in Oil Production Systems, Annual SPE Technical Conference (ATCE 2008) (Denver, CO Sep. 2008), Proceedings 2008 (ISBN 978-1-55563-147-5; SPE-115665).
Kennicutt, M.C. III, et al., Relation Between Shallow Sediment Bitumens and Deeper Reservoired Hydrocarbons, Offshore Santa Maria Basin, California, U.S.A., Appl. Geochem. v. 3, No. 6, pp. 573-582, Nov.-Dec. 1988.
Asomaning, S., Test Methods for Determining Asphaltene Stability in Crude Oils, AIChE Spring Nat. Mtg. (New Orleans, LA, Mar. 2002) Pap; Petrol. Sci. Technol. v. 21, Nos. 3-4, pp. 581-590 (ISSN 1091-6466).

Thompson, K.F.M., Aspects of Petroleum Basin Evolution Due to Gas Advection and Evaporative Fractionation, Organic Geochemistry 41 (4), pp. 370-385, 2010.
Thompson, K.F.M., Mechanisms Controlling Gas and Light End Composition in Pyrolysates and Petroleum: Applications in the Interpretation of Reservoir Fluid Analyses, Organic Geochemistry 37 (7), pp. 798-817 2006.
Thompson, K.F.M., Gas-Condensate Migration and Oil Fractionation in Deltaic Systems, Marine and Petroleum Geology 5 (3), pp. 237-246 1988.
Murty, C.R.K, et al., Fluid Transfer Mechanism Using Geochemistry in Shallow Oil Zones of Bahrain Oil Field, SPE Middle East Oil and Gas Show and Conference, MEOS, Proceedings , pp. 591-596, 2005.
Thompson, K.F.M., Compositional Regularities Common to Petroleum Reservoir Fluids and Pyrolysates of Asphaltenes and Kerogens, Organic Geochemistry 33 (7), pp. 829-841 2002.
Thompson, K.F.M., A Classification of Petroleum on the Basis of the Ratio of Sulfur to Nitrogen, Organic Geochemistry 21 (8-9), pp. 877-890 1994.
Thompson, K.F.M., et al., Correlations of Gulf Coast Petroleums on the Basis of Branched Acyclic Alkanes, Organic Geochemistry 18 (1), pp. 103-119, 1992.
Thompson, K.F.M., Fractionated Aromatic Petroleums and the Generation of Gas-Condensates, Organic Geochemistry 11 (6), pp. 573-590 1987.
Kissin, Y.V., Catagenesis of Light Aromatic Compounds in Petroleum, Organic Geochemistry 29 (4), pp. 947-962 1998.
Kissin, Y.V., Chemical Mechanism of Hydrocarbon Cracking Over Solid Acidic Catalysts, Journal of Catalysis 163 (1), pp. 50-62 1996.
Kissin, Y.V., Molecular Weight Distributions of Linear Polymers: Detailed Analysis From GPC Data, Journal of Polymer Science, Part A: Polymer Chemistry 33 (2), pp. 227-237 1995.
Kissin, Y.V., Degenerate Non-Primary Products in Catalytic Cracking of Isoalkanes, Journal of Catalysis 146 (2), pp. 358-369 1994.
Kissin, Y.V., Catagenesis of Light Acyclic Isoprenoids in Petroleum, Organic Geochemistry 20 (7), pp. 1077-1090 1993.
Kissin, Y.V., Relative Reactivities of Alkanes in Multi-Component Catalytic Cracking Reactions, Catalysis Letters 19 (2-3), pp. 181-187 1993.
Kissin, Y.V., Primary Products in Catalytic Cracking of Alkanes: Quantitative Analysis, Journal of Catalysis 132 (2), pp. 409-421 1991.
Kissin, Y.V., Ethylene Oligomerization and Chain Growth Mechanisms With Ziegler-Natta Catalysts, Macromolecules 26 (9), pp. 2151-2158 1993.
Kissin, Y.V., Infrared Method for Measuring Orientation in Polyethylene Films, Journal of Polymer Science, Part B: Polymer Physics 30 (10), pp. 1165-1172 1992.
Kissin, Y.V., et al., 13C NMR Spectra of Propylene/1-Hexene Copolymers, Macromolecules 24 (9), pp. 2632-2633 1991.
Kissin, Y.V., Relative Reactivities of Alkanes in Catalytic Cracking Reactions, Journal of Catalysis 126 (2), pp. 600-609 1990.
Kissin, Y.V., Catagenesis of Light Cycloalkanes in Petroleum, Organic Geochemistry 15 (6), pp. 575-594 1990.
Kissin, Y.V., Acyclic Components in Dewaxed Heavy Distillates, Fuel 69 (10), pp. 1283-1291 1990.
Kissin, Y.V., Catagenesis and Composition of Petroleum: Origin of N-Alkanes and Isoalkanes in Petroleum Crudes, Geochimica et Cosmochimica Acta 51 (9), pp. 2445-2457 1987.
Kissin, Y.V., Co-Oligomerization of Ethylene and Higher Linear Alpha Olefins. I. Co-Oligomerization With the Sulfonated Nickel Ylide-Based Catalytic System, Journal of Polymer Science, Part A: Polymer Chemistry 27 (2), pp. 605-621 1989.
Kissin, Y.V., Co-Oligomerization of Ethylene and Higher Linear Alpha Olefins. II. Olefin Reactivities in Various Reaction Steps of Co-Oligomerization With Nickel Ylide-Based System, Journal of Polymer Science, Part A: Polymer Chemistry 27 (2), pp. 623-637.
Kissin, Y.V., 'Homogeneous' Interpretation of Ethylene Polymerization Kinetics With Supported Ziegler-Natta Catalysts, Journal of Molecular Catalysis 56 (1-3 pt 2), pp. 220-236 1989.

(56) References Cited

OTHER PUBLICATIONS

Kissin, Y.V. Oligomerization of Ethylene With a Homogeneous Sulfonated Nickel Ylide-Aluminum Alkoxide Catalys, Journal of Polymer Science, Part A: Polymer Chemistry 27 (1), pp. 147-155 1988.

Kissin, Y.V., Free-Radical Reactions of High Molecular Weight Isoalkanes, Industrial and Engineering Chemistry Research 26 (8), pp. 1633-1638 1987.

Kissin, Y.V., A Novel Multifunctional Catalytic Route for Branched Polyethylene Synthesis, Studies in Surface Science and Catalysis 25 (C), pp. 443-460 1986.

Meulbroek, Peter, et. al., Phase Fractionation At South Eugene Island Block 330, Org. Geochem. vol. 29, No. 1-3, pp. 223-239, 1998.

| Species | MW | | Raw Data | Normalized wt% | Calculated Mole % | C17-27 Normalized |
|---|---|---|---|---|---|---|
| | | Sample ID | US039224 | US039224 | US039224 | US039224 |
| | | Depth | 8357.2 | 8357.2 | 8357.2 | 8357.2 |
| | | Sample Type | SWC | SWC | SWC | SWC |
| | | File | G1010567.D | G1010567.D | G1010567.D | G1010567.D |
| CO2 | 44.01 | | | | | |
| H2S | 34.08 | | | | | |
| N2 | 28.01 | | | | | |
| C1 | 16.04 | | | | | |
| C2 | 30.07 | | | | | |
| C3 | 44.10 | | | | | |
| iC4 | 58.12 | IC4 | 0 | 0 | 0 | 0 |
| nC4 | 58.12 | NC4 | 0 | 0 | 0 | 0 |
| iC5 | 72.15 | IC5 | 0 | 0 | 0 | 0 |
| nC5 | 72.15 | NC5 | 0 | 0 | 0 | 0 |
| C6 | 86.18 | NC6 | 0 | 0 | 0 | 0 |
| C7 | 100.20 | NC7 | 0 | 0 | 0 | 0 |
| C8 | 114.23 | NC8 | 0 | 0 | 0 | 0 |
| C9 | 128.26 | NC9 | 28912 | 1.608 | 2.938 | 8.269 |
| C10 | 142.29 | NC10 | 68379 | 3.803 | 6.263 | 17.629 |
| C11 | 156.31 | NC11 | 108572 | 6.038 | 9.051 | 25.479 |
| C12 | 170.34 | NC12 | 116213 | 6.463 | 8.891 | 25.026 |
| C13 | 184.37 | NC13 | 127584 | 7.096 | 9.018 | 25.385 |
| C14 | 198.39 | NC14 | 127207 | 7.075 | 8.355 | 23.520 |
| C15 | 212.42 | NC15 | 131700 | 7.325 | 8.079 | 22.743 |
| C16 | 226.43 | NC16 | 114142 | 6.348 | 6.569 | 18.491 |
| C17 | 240.46 | NC17 | 110913 | 6.169 | 6.011 | 16.920 |
| C18 | 254.46 | NC18 | 96506 | 5.367 | 4.942 | 13.912 |
| C19 | 268.51 | NC19 | 91476 | 5.088 | 4.439 | 12.497 |
| C20 | 282.54 | NC20 | 86592 | 4.816 | 3.994 | 11.242 |
| C21 | 296.56 | NC21 | 75609 | 4.205 | 3.322 | 9.352 |
| C22 | 310.59 | NC22 | 70296 | 3.910 | 2.949 | 8.302 |
| C23 | 324.61 | NC23 | 65527 | 3.644 | 2.631 | 7.405 |
| C24 | 338.64 | NC24 | 59077 | 3.286 | 2.273 | 6.399 |
| C25 | 352.67 | NC25 | 53480 | 2.974 | 1.976 | 5.563 |
| C26 | 366.69 | NC26 | 46781 | 2.602 | 1.661 | 4.676 |
| C27 | 380.72 | NC27 | 38724 | 2.154 | 1.325 | 3.731 |
| C28 | 394.74 | NC28 | 30648 | 1.705 | 1.012 | 2.848 |
| C29 | 408.77 | NC29 | 29447 | 1.638 | 0.939 | 2.643 |
| C30 | 422.80 | NC30 | 22423 | 1.247 | 0.691 | 1.945 |
| C31 | 436.82 | NC31 | 18230 | 1.014 | 0.544 | 1.531 |
| C32 | 450.85 | NC32 | 13431 | 0.747 | 0.388 | 1.093 |
| C33 | 464.87 | NC33 | 18130 | 1.008 | 0.508 | 1.431 |
| C34 | 478.90 | NC34 | 11749 | 0.653 | 0.320 | 0.900 |
| C35 | 492.93 | NC35 | 9506 | 0.529 | 0.251 | 0.707 |
| C36 | 506.95 | NC36 | 7518 | 0.418 | 0.193 | 0.544 |
| C37 | 520.98 | NC37 | 5862 | 0.326 | 0.147 | 0.413 |
| C38 | 535.00 | NC38 | 5018 | 0.279 | 0.122 | 0.344 |
| C39 | 549.03 | NC39 | 4315 | 0.240 | 0.102 | 0.288 |
| C40 | 563.06 | NC40 | 4086 | 0.227 | 0.095 | 0.266 |
| | | SUM | 1798053 | 100.000 | 100.000 | |
| | | Sum C17-27 | | | 35.525 | 100.000 |
| | | A Coefficient | | | | 190.5855 |
| | | B Exponent Factor | | | | -0.1428 |
| | | R^2 goodness of fit | | | | 0.9942 |
| | | Link to graph | | | | Graph |

FIG. 7

PETROLEUM-FLUID PROPERTY PREDICTION FROM GAS CHROMATOGRAPHIC ANALYSIS OF ROCK EXTRACTS OR FLUID SAMPLES

CROSS-REFERENCE TO RELATED APPLICATIONS

This application claims the benefit of priority to U.S. provisional application No. 61/679,311, filed on Aug. 3, 2012, the contents of which are herein incorporated by reference.

STATEMENT REGARDING FEDERALLY SPONSORED RESEARCH

None.

FIELD OF THE INVENTION

Methods for predicting subsurface fluid properties (e.g., petroleum phase or API gravity) using small volumes (microliter or milligram scale) from subsurface rock samples are described. In one embodiment, the method is applied to petroleum liquid samples where drilling fluid or other contaminants can hinder accurate direct property measurements.

BACKGROUND OF THE INVENTION

Direct measurement of petroleum API gravity or petroleum phase can be extremely difficult to obtain from rock samples taken from a subsurface well where fluid tests (e.g., drill stem tests (DST), modular dynamic tests (MDT), repeat formation tests (RFT), etc.) are not economically feasible, or not available. However, fluid property information (e.g., API gravity, fluid phase) is often important for evaluating and planning well or field development and further exploration. Rock samples (e.g., sidewall cores, core, or cuttings) are often readily available but typically do not contain enough petroleum to perform actual measurements of relevant properties.

There are several previously known methods for analyzing alkanes and pseudo-components from well tests or production petroleum fluids (oils or condensates) (Katz and Firoozabadi, 1978; Pedersen and Christensen, 2007). Proper measurement of fluid properties and recognition of fluid phase can be highly dependent on whether sufficient volume is available (~5-100 milliliters). Unfortunately, these methods do not work well for smaller sample volumes. Previous methods have used biomarker analysis, gas chromatography/mass spectrometry (GCMS), and/or gas chromatography/tandem mass spectrometry (GCMSMS) to constrain oil quality by one of several approaches. For example, biomarker ratios can either be directly correlated to an oil quality parameter (i.e., API gravity) or combined by a statistical approach to determine oil quality (Hughes and Holba, 1988; Smalley et al., 1996; Michael, 2003; Huizinga et al., 2007). Biomarker parameters may also be used to constrain oil type (e.g., low sulfur-low asphaltene, medium sulfur-medium asphaltene, or high sulfur-high asphaltene contents) and/or thermal maturity (maximum temperature experienced). Once the oil type and maturity are established, Pressure-Viscosity-Temperature (PVT) reports for similar oils may be used to estimate probable oil properties. Other methods include pyrolysis of rock samples by Rock-Eval pyrolysis (Holba et al., 2004; Dow et al., 2001; Dow and Talukdar, 1991; Baskin and Jones, 1993) or pyrolytic oil-productivity index (POPI) method (Jones and Tobey, 1999; Jones et al., 2004; Jones and Halpern, 2007) can provide proportion of light fluid versus pyrolyzed product from heavy oil components, which in turn can be correlated with bulk fluid properties. Pyrolysis methods can work best for heavy oils (API<25). Oil quality predictions have been attempted using well logging techniques such as NMR or CMR logging (Zhang et. al., 1998).

Some previous methods for predicting oil quality have certain disadvantages. As alluded earlier, quality of measurements in some previous methods can be significantly limited by amount of sample available. In some cases, rock samples (sidewall cores, cores, or cuttings) may only contain trace amounts of petroleum (microgram to milligram amounts). In other situations, oil samples may be available but can be hampered by contamination issues with drilling fluids. Biomarker methods usually require extensive analysis and interpretation and are relatively more expensive and time consuming than gas chromatography. Moreover, biomarker methods work well for black oils but often do not work well for light oil or condensate contributions to an accumulation which contain little or no biomarkers.

BRIEF SUMMARY OF THE DISCLOSURE

This disclosure details the use of geochemical high resolution gas chromatographic data with concepts of fluid phase behavior to predict petroleum properties (e.g., API gravity or petroleum phase). Gas chromatography analysis is relatively inexpensive (half the cost of GCMS biomarker analysis), and can be performed on a small volume of oil or extracted oil from a rock source.

In one embodiment, subsurface petroleum-fluid properties (e.g., phase and API gravity) are predicted using gas-chromatographic data for a small-volume sample, either extracted from a sub-surface reservoir or obtained from a contaminated fluid sample. Small volume equates to microliter scale volumes (or milligram scale weights) from the above sample types, where a fluid test may not be available for analysis, an insufficient amount of sample is available for proper API gravity measurement (ASTM standards), or the sample contains non-endemic compounds interfering with an accurate API gravity determination of the petroleum.

In another embodiment, gas chromatographic data is calibrated against measured petroleum properties of sample taken from a similar source rock type. The calibration can be performed by taking measurements on local oil samples taken from a petroleum system closely related or same by affinity to the source rock type. Source types can be determined by various geochemical properties (e.g., oil bulk properties, biomarkers, or isotopes) that are specific to a geologic province or to a geologic province type. Thus, petroleum-type calibrations across multiple basins can be used. Global petroleum property predictions are also potentially possible using multi-variate equations that include the methods described herein, coupled with other geochemical data (e.g., SARA analyses). When physical processes cause exceptional deviations of oil properties from source type control, additional terms can be added to this method to account for these exceptional deviations.

The methods described herein work for various petroleum samples including petroleum samples with decreasing n-alkane intensity (concentration) as carbon number increases. The methods may also be applied to petroleum samples of any maturity including, but not limited to, lower maturity, middle oil-window, or high thermal maturity samples.

In some embodiments, the methods can be applied to new fresh rock samples or old stored rock samples. Side wall core, core chips (preferably from core interior), or cuttings samples (in order of preference) can be used. Fresh sidewall core that have been washed upon reaching the surface, followed by immediate preservation against loss of light hydrocarbons by freezing or refrigeration are optimum. Old samples that have been stored for long periods of time (1 to 20+ years) can suffer from extreme evaporation. The method can still be applied if the higher molecular weight alkanes are representative of the light alkanes. Mixtures of light and heavy contributing oils may have more than one trend.

In one embodiment, a method of analyzing reservoir fluid property comprises: a) obtaining a rock extract or fluid sample from a subterranean reservoir; b) analyzing the rock extract or fluid sample by gas chromatography to provide a gas chromatogram; c) calculating chromatographic peak area for three or more alkanes in the gas chromatogram; d) selecting a representative series of three or more alkane peaks for analysis; e) optionally, normalizing the alkane peak areas across the representative series; f) optionally, converting the chromatographic peak areas of the selected series to mole percent or weight percent; g) obtaining a plot of the concentration in terms of peak area, mole percent or weight percent, against carbon number or molecular weight; h) fitting an equation to plotted concentrations obtained from (g); i) determining goodness of fit ($R^2$) for the equation to the plotted peaks; j) re-selecting the representative series of alkane peaks and repeating (e), (f), (g), (h), (i) and (j) as needed to obtain suitable goodness of fit; k) identifying calibration petroleum sample or samples with similar plot; and l) assigning one or more fluid properties from the calibration petroleum sample or samples to the rock extract or fluid sample with unknown property.

In another embodiment, a method of analyzing reservoir fluid property comprises: a) obtaining a rock extract or fluid sample from a subterranean reservoir; b) analyzing the rock extract or fluid sample by gas chromatography to provide a gas chromatogram; c) calculating chromatographic area for three or more alkane pseudocomponents in the gas chromatogram; d) selecting a representative series of three or more pseudocomponent areas for analysis; e) optionally, normalizing the pseudocomponent peak areas across the representative series; f) optionally, converting the pseudocomponent peak areas of the selected series to mole percent or weight percent; g) obtaining a plot of the concentration in terms of pseudocomponent peak area, mole percent or weight percent against carbon number or molecular weight; h) fitting an equation to plotted concentrations obtained from (g); i) determining goodness of fit (R2) for the equation to the pseudocomponent areas; j) re-selecting the representative series of pseudocomponent areas and repeating (e), (f), (g), (h), (i) and (j) as needed to obtain suitable goodness of fit; k) identifying a calibration petroleum sample with similar plot; and l) assigning one or more fluid properties from the calibration petroleum sample to the rock extract or fluid sample with unknown properties.

In yet another embodiment, a method of analyzing reservoir fluid property comprising: a) obtaining a contaminated, degraded or evaporated rock extract or fluid sample from a subterranean reservoir; b) analyzing the contaminated, degraded or evaporated rock extract or fluid sample by gas chromatography to provide a gas chromatogram; c) calculating chromatographic area for three or more alkane areas in the gas chromatogram; d) selecting a representative series of three or more alkane areas for analysis; e) optionally, normalizing the alkane peak areas across the representative series; f) optionally, converting the chromatographic peak areas of the selected series to mole percent or weight percent; g) obtaining a plot of the concentration in terms of peak area, mole percent or weight percent against carbon number or molecular weight; h) fitting an equation to plotted concentrations obtained from (g); i) determining goodness of fit (R2) for the equation to the plotted peaks; j) re-selecting the selected series of alkane areas and repeating (e), (f), (g), (h), (i) and (j) as needed to obtain suitable goodness of fit; k) identifying a calibration petroleum sample with similar plot; and l) assigning one or more fluid properties from the calibration petroleum sample to the contaminated, degraded or evaporated rock extract or fluid sample with unknown property.

The methods described may be performed with a fluid extracted from a rock sample, a fluid sample retrieved from a subterranean reservoir, a highly evaporated rock extract or fluid sample, a fluid sample of an oil or a condensate from a gas phase, a fluid sample containing mixed condensate and residual oil sample, a fluid sample of condensates from carbonate sources, a fluid sample from marine shale derived condensates, a fluid sample from condensates with exceptional high API, a fluid sample from a contaminated oil, or a mixed fluid sample.

Additionally, the methods above may be performed by selecting representative series of alkanes or pseudocomponents peaks or areas between $C_8$ and $C_{35}$ that may include three or more peaks between $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, and $C_{35}$. Frequently the representative series of alkanes or pseudocomponents peaks or areas may be alkane molecular weights from approximately $C_8$-$C_{12}$, $C_{10}$-$C_{14}$, $C_{10}$-$C_{15}$, $C_{10}$-$C_{16}$, $C_{10}$-$C_{17}$, $C_{10}$-$C_{18}$, $C_{10}$-$C_{19}$, $C_{10}$-$C_{20}$, $C_{10}$-$C_{21}$, $C_{10}$-$C_{22}$, $C_{10}$-$C_{23}$, $C_{10}$-$C_{24}$, $C_{10}$-$C_{25}$, $C_{10}$-$C_{26}$, $C_{10}$-$C_{27}$, $C_{10}$-$C_{30}$, $C_{10}$-$C_{32}$, $C_{10}$-$C_{34}$, $C_{10}$-$C_{36}$, $C_{10}$-$C_{37}$, $C_{12}$-$C_{14}$, $C_{12}$-$C_{15}$, $C_{12}$-$C_{16}$, $C_{12}$-$C_{17}$, $C_{12}$-$C_{18}$, $C_{12}$-$C_{19}$, $C_{12}$-$C_{20}$, $C_{12}$-$C_{21}$, $C_{12}$-$C_{22}$, $C_{12}$-$C_{23}$, $C_{12}$-$C_{24}$, $C_{12}$-$C_{25}$, $C_{12}$-$C_{26}$, $C_{12}$-$C_{27}$, $C_{12}$-$C_{30}$, $C_{12}$-$C_{32}$, $C_{12}$-$C_{34}$, $C_{12}$-$C_{36}$, $C_{12}$-$C_{37}$, $C_{14}$-$C_{16}$, $C_{14}$-$C_{17}$, $C_{14}$-$C_{18}$, $C_{14}$-$C_{19}$, $C_{14}$-$C_{20}$, $C_{14}$-$C_{21}$, $C_{14}$-$C_{22}$, $C_{14}$-$C_{23}$, $C_{14}$-$C_{24}$, $C_{14}$-$C_{25}$, $C_{14}$-$C_{26}$, $C_{14}$-$C_{27}$, $C_{14}$-$C_{30}$, $C_{14}$-$C_{32}$, $C_{14}$-$C_{34}$, $C_{14}$-$C_{36}$, $C_{14}$-$C_{37}$, $C_{15}$-$C_{17}$, $C_{15}$-$C_{18}$, $C_{15}$-$C_{19}$, $C_{15}$-$C_{20}$, $C_{15}$-$C_{21}$, $C_{15}$-$C_{22}$, $C_{15}$-$C_{23}$, $C_{15}$-$C_{24}$, $C_{15}$-$C_{25}$, $C_{15}$-$C_{26}$, $C_{15}$-$C_{27}$, $C_{15}$-$C_{30}$, $C_{15}$-$C_{32}$, $C_{15}$-$C_{34}$, $C_{15}$-$C_{36}$, $C_{15}$-$C_{37}$, $C_{17}$-$C_{19}$, $C_{17}$-$C_{20}$, $C_{17}$-$C_{21}$, $C_{17}$-$C_{22}$, $C_{17}$-$C_{23}$, $C_{17}$-$C_{24}$, $C_{17}$-$C_{25}$, $C_{17}$-$C_{26}$, $C_{17}$-$C_{27}$, $C_{17}$-$C_{30}$, $C_{17}$-$C_{32}$, $C_{17}$-$C_{34}$, $C_{17}$-$C_{36}$, $C_{17}$-$C_{37}$, $C_{16}$-$C_{21}$, $C_{18}$-$C_{21}$, $C_{19}$-$C_{21}$, $C_{21}$-$C_{23}$, $C_{21}$-$C_{24}$, $C_{21}$-$C_{25}$, $C_{21}$-$C_{26}$, $C_{21}$-$C_{27}$, $C_{21}$-$C_{30}$, $C_{21}$-$C_{32}$, $C_{21}$-$C_{34}$, $C_{21}$-$C_{36}$, $C_{21}$-$C_{37}$, $C_{16}$-$C_{22}$, $C_{18}$-$C_{22}$, $C_{19}$-$C_{22}$, $C_{20}$-$C_{22}$, $C_{22}$-$C_{24}$, $C_{22}$-$C_{25}$, $C_{22}$-$C_{26}$, $C_{22}$-$C_{27}$, $C_{22}$-$C_{30}$, $C_{22}$-$C_{32}$, $C_{22}$-$C_{34}$, $C_{22}$-$C_{36}$, $C_{22}$-$C_{37}$, $C_{16}$-$C_{23}$, $C_{18}$-$C_{23}$, $C_{19}$-$C_{23}$, $C_{20}$-$C_{23}$, $C_{23}$-$C_{25}$, $C_{23}$-$C_{26}$, $C_{23}$-$C_{27}$, $C_{23}$-$C_{30}$, $C_{23}$-$C_{32}$, $C_{23}$-$C_{34}$, $C_{23}$-$C_{36}$, $C_{23}$-$C_{37}$, and the like.

Representative chromatographic spectra may be stored in a spreadsheet program such as EXCEL™ commercially available from Microsoft Corp. (Bellevue, Wash.), column separated value, tab separated value, hypertext machine language, relational database, text or other format of storing chromatographic spectra.

BRIEF DESCRIPTION OF THE DRAWINGS

A more complete understanding of the present invention and benefits thereof may be acquired by referring to the follow description taken in conjunction with the accompanying drawings in which:

FIG. 7: Example calculations showing actual data for a SWC extract from an oil stained sandstone.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

The present invention provides an inexpensive, rapid, and easily interpreted analysis of petroleum fluid quality. This analysis can be used to speed decisions and improve the quality and quantity of information available for reservoir engineers. Other advantages of the present invention will be apparent from the disclosure herein.

Figure 1:
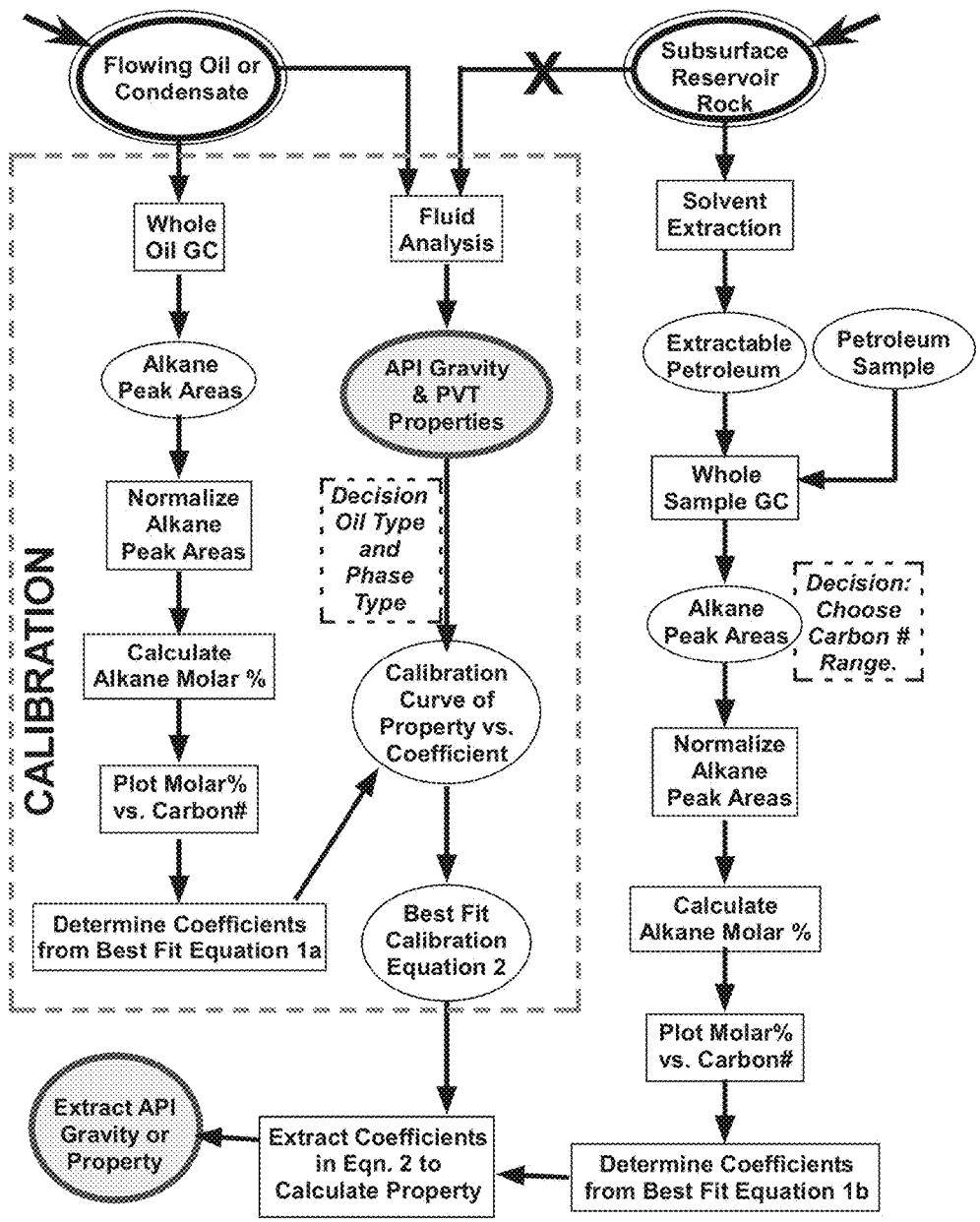
FIG. 1: Flow chart for calibration and application.
Figure 2A:
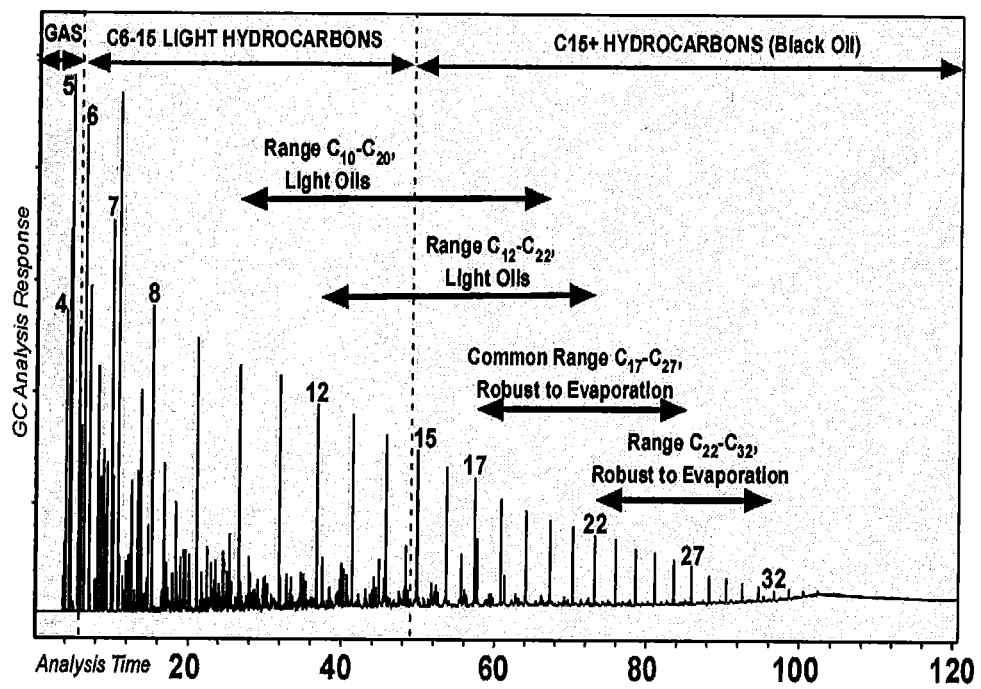
FIG. 2: A) Gas chromatographic profile of an oil sample; B) Gas chromatographic profile of a rock extract from a frozen sandstone core sample from a reservoir zone of an oil field; C) Gas chromatographic profile that defines pseudocomponents for an oil.
Figure 2B:
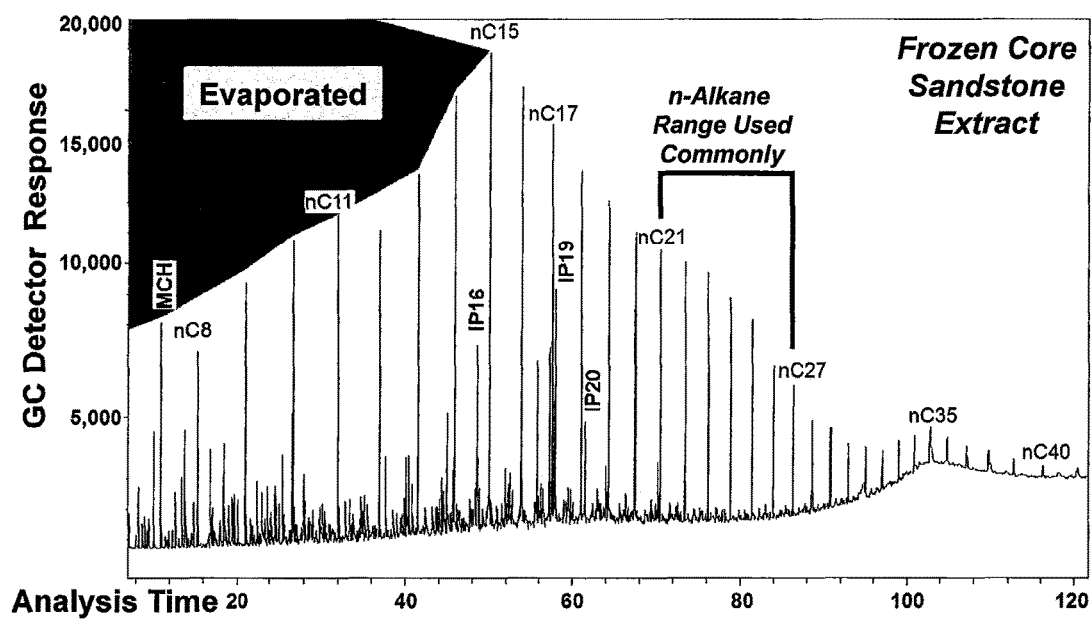

In one embodiment, a general flow chart for calibration and application of the method is shown in FIG. 1. The present invention uses small volume extracts of rock samples, and determines the gas chromatographic profile of n-alkanes in the rock extract or oil sample (FIGS. 2A and 2B). The pattern is compared with patterns of petroleums of known fluid properties (i.e., API gravity or petroleum phase) to determine the properties of the fluid in the rock sample.

Figure 2C:
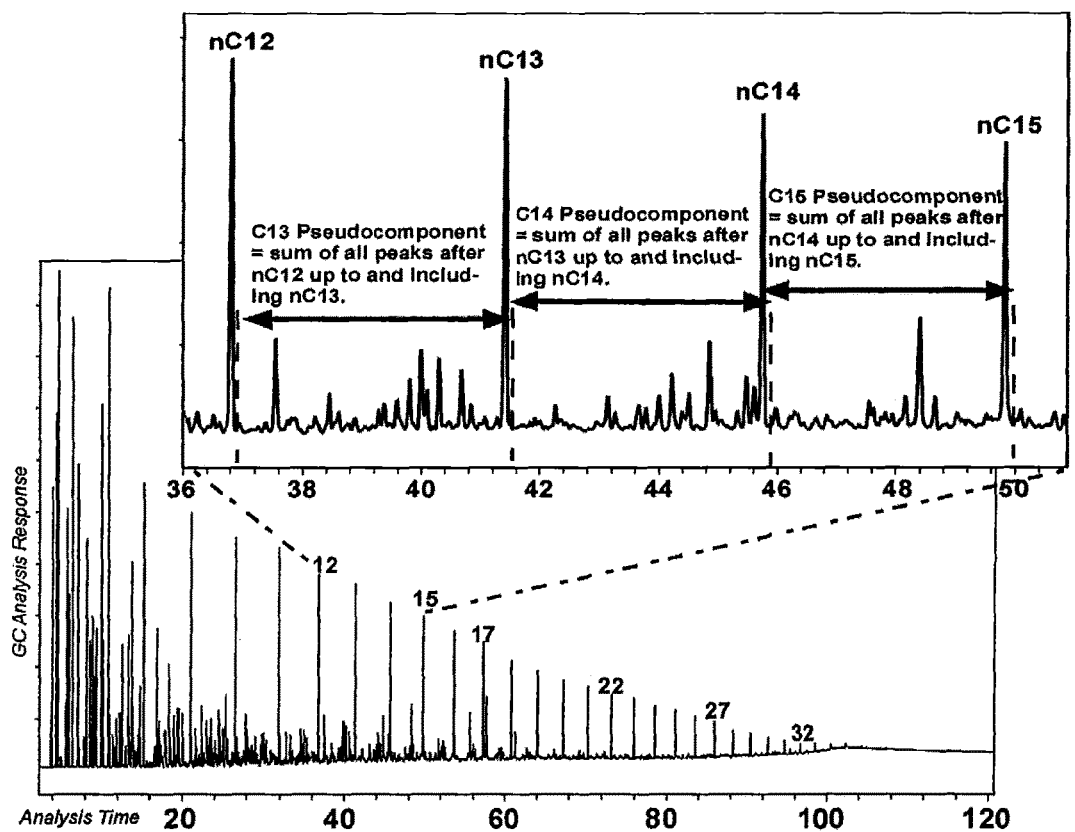

A rock extract or contaminated fluid is analyzed by gas chromatography. In the simplest method, peak areas are measured for the alkanes of interest (usually n-alkanes) and a carbon range is selected that is appropriate to the sample. The raw data is entered into an automated spreadsheet to facilitate fast and efficient processing of data for large or small numbers of samples. However, pseudocomponents may be used instead of a single n-alkane. Each pseudocomponent is the sum all peaks between n-alkanes and including the highest carbon number n-alkane, (See FIG. 2C). In other embodiments, other analytical techniques may be used to obtain concentration information in lieu of gas chromatography.

Figure 3:
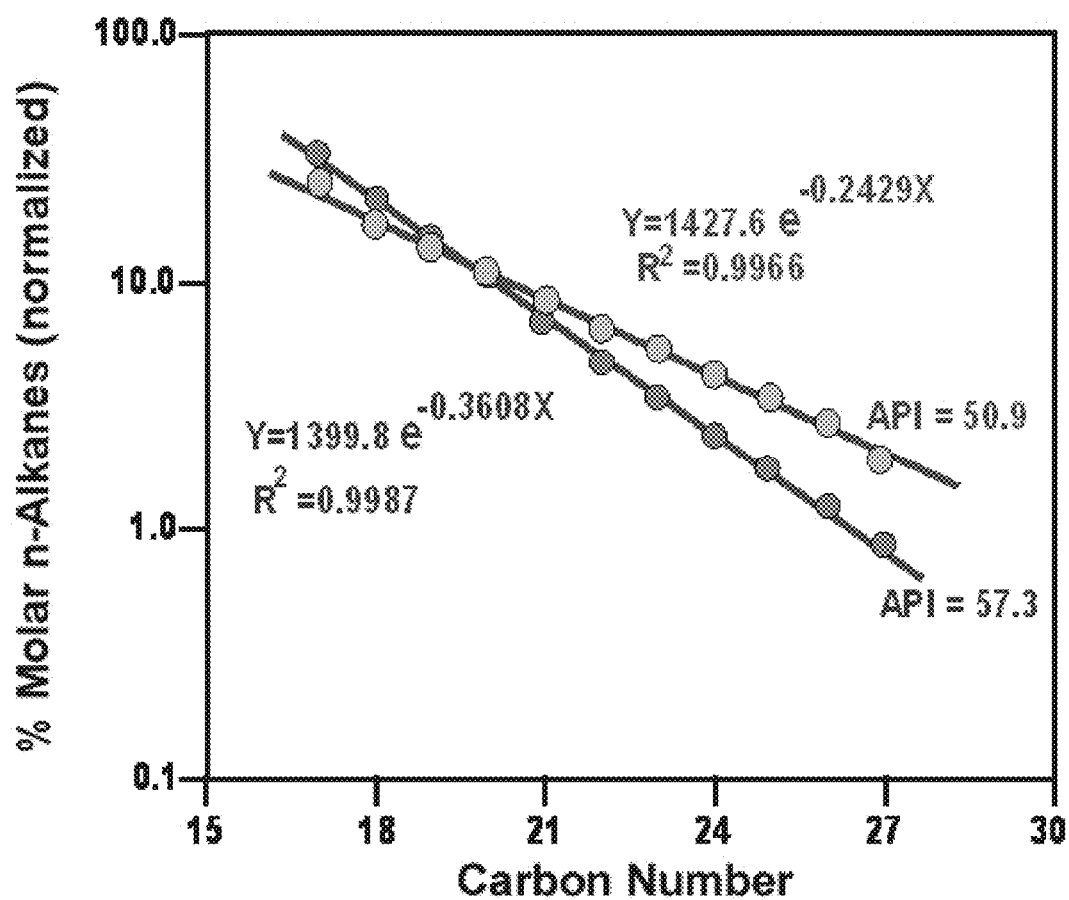
FIG. 3: Plot of normalized percent molar n-alkane concentration on a log scale versus n-alkane carbon number. Plots as shown are constructed for oils or condensates. Slope is a function of API gravity.

The data for a range of n-alkanes is normalized (e.g., $C_{17}$-$C_{27}$ is normally used to avoid evaporation in the rock extract of light alkanes and capture information on major contributors to petroleum, but for some samples ranges of $C_8$-$C_{20}$, $C_{12}$-$C_{22}$ or $C_{22}$-$C_{32}$ may be advantageous. For light oils and condensates an n-alkane range like $C_{12}$-$C_{22}$ may be advantageous (the range can be adjusted to lower or higher carbon number range to fit petroleum characteristics). Extracts of rocks that have been stored under less than optimal conditions and that have experienced extensive evaporation of light hydrocarbons, may be best evaluated by an alkane range like $C_{22}$-$C_{32}$. The normalized data is converted to molar percent in a spreadsheet using industry accepted molecular weights (Katz and Firoozabadi, 1978). The molar percent of each alkane is plotted on a log scale vs. the carbon number for that alkane (FIG. 3) within the spreadsheet. The result should be a straight line and the best fit equation through that line may be of the form of equation 1, where A and B=coefficients and x=carbon number or carbon number molecular weight.

$$n\text{-Alkane Mole \%} = A\, e^{-Bx} \tag{1}$$

If the goodness of fit ($R^2$) is less than 0.98 because of contamination, peak co-elutions, specious measurement, component loss, or some other unknown reason; then the spreadsheet allows for editing of the n-alkane or alkanes normalized molar percent affected by the contaminant to improve the mathematic fit and the most representative A and B coefficients. This editing feature allows for prediction of properties of contaminated oil samples.

Figure 4:
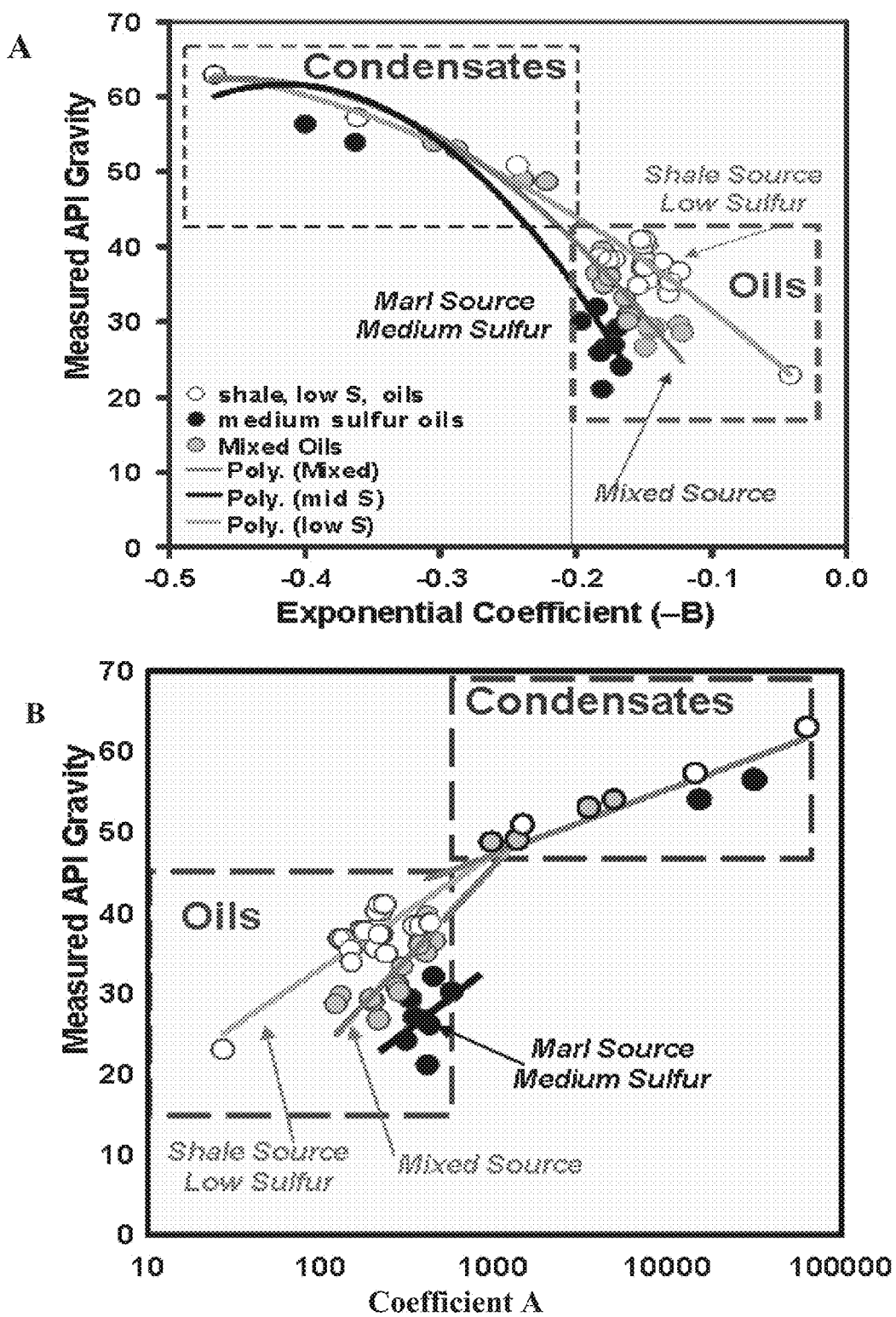
FIG. 4: A) Calibration curve using the exponential coefficient B for Basin A with two end member oil types and a mixed oil type of the two end member oil types. B) Calibration curve using the coefficient A for Basin A with two end member oil types and a mixed oil type of the two end member oil types. A best fit equation is constructed for both A and B factors for each source type. For unknowns the predicted API is calculated from these equations using the A and B factors.

Coefficients A and B are proportional to fluid properties, thus, calibration plots of each coefficient versus measured fluid property (e.g., API gravity) of known oils can be plotted such that the best fit of these later plots produces calibration equations. The optimum calibration plot is constructed from data for oils from the same petroleum system as the unknown sample (rock or oil), usually from the same geologic area or basin. FIGS. 4A and 4B show examples of calibration curves for geologic basin "A" with two oil types and a mixed oil type of the two end members. A more general series of global calibration curves can also be constructed for different petroleum types (see example in FIG. 9). Once calibration equations are available, then coefficients for unknowns may be substituted into the calibration equations and a predicted fluid property calculated (e.g., API gravity).

Oil types may be described as containing (1) high asphaltenes with high sulfur; (2) medium asphaltene content with medium sulfur; (3) low asphaltenes with low sulfur content; or (4) very low asphaltene content. Another factor which can affect oil type is thermal maturity (i.e., the highest temperature that a petroleum has experienced or the length of time it has been heated in the subsurface). Multiple geologic and compositional factors may combine to affect the relationship of molecular distribution and petroleum property.

The petroleum fluid phase may be recognized by the magnitude of the coefficients. Thus Basin A petroleum (FIGS. 4A and 4B) from a low-sulfur shale derived subsurface liquid phase will have −B>0.185 and A>700. Condensates will have −B<0.205 and A<550. The petroleum phase predictions may show slightly different ranges for the "A" and "B" factors in other basins, but the cutoffs are derivable from the observed phase of fluids in the specific calibration set. For the low sulfur and low asphaltene family of oils in FIGS. 4A-4B plot of API gravity versus the coefficients (log scale for coefficient A and linear scale for B) allows illustration that the values of the coefficients may be used to predict whether the fluid is an oil or a condensate from a gas phase (FIGS. 5A and 5B).

Figure 5:
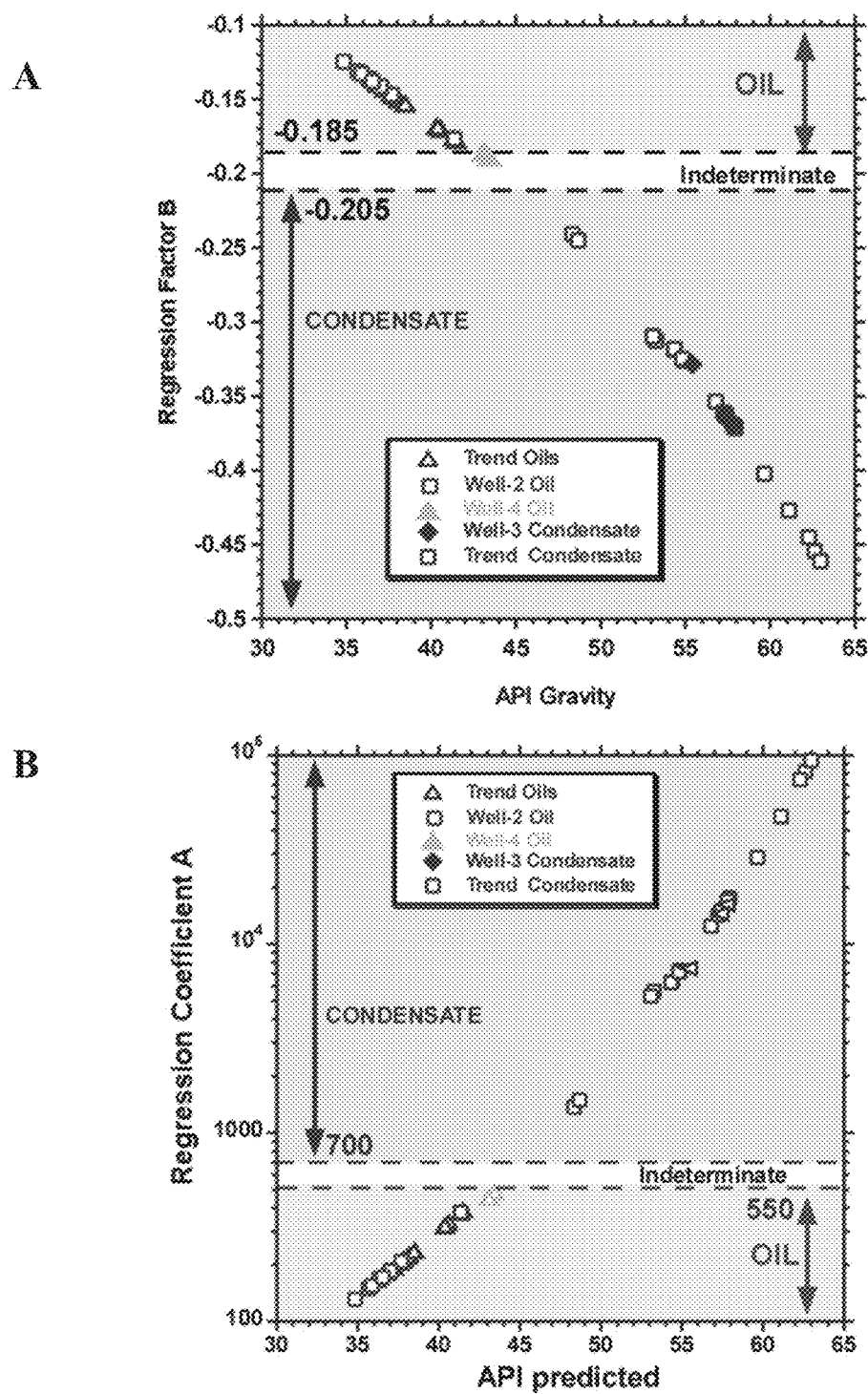
FIG. 5: A) Petroleum phases may be discriminated by coefficient B magnitude. B) Petroleum phases may be discriminated by coefficient A magnitude. Illustration of the phase cutoffs of coefficients A and B for low-sulfur (low asphaltene) shale source for a specific area, Basin A (see FIG. 4).

Note, one sample from a gas field plots with the oil trend in FIG. 5. This occurred because during testing a high pressure drop around the well caused condensate to form as a liquid phase. This liquid phase extracted a residual oil in the small pores of the reservoir rock. The combined condensate+residual oil exists as an oil phase.

Spreadsheet Automation

All calculations were combined into a series of spreadsheets that automate calculations so that large numbers of sample data can be processed. When contaminants or oil constituents other than n-alkanes co-elute in the gas chromatogram with peaks of interest, then plot visualization, and an editing process was also automated into the spreadsheets.

In one embodiment, measured n-alkane peaks and pseudo-component molecular weights are used to calculate molar percent because n-alkanes provide large, easily quantified peaks. In another embodiment, n-alkane areas and n-alkane molecular weights or pseudo-component areas and pseudo-component molecular weights work equally well and any reasonable molecular weight may be used. In yet another embodiment, a correlation using simple weight percent could have also been used if done in a consistent manner.

Example

Figure 6:
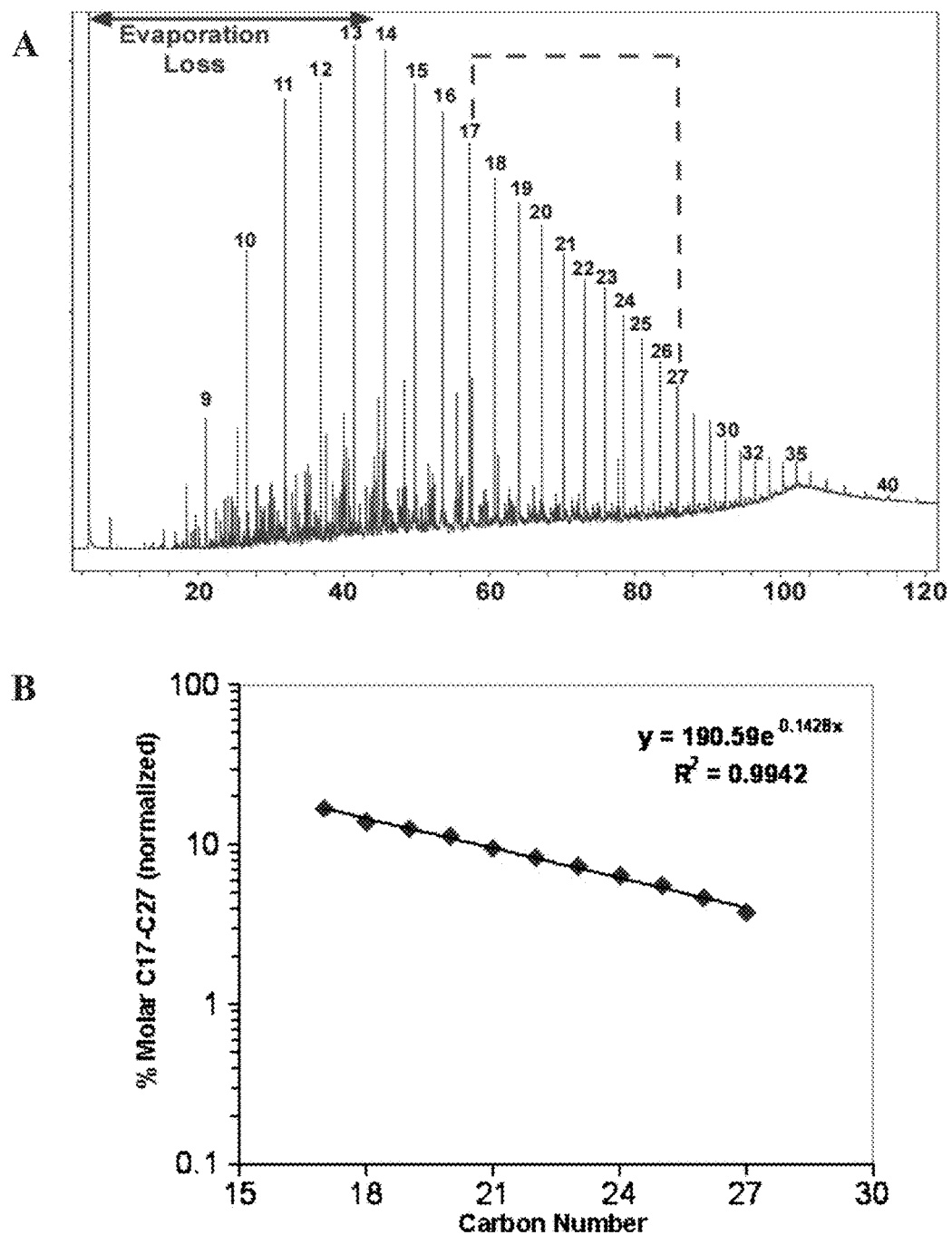
FIG. 6: A) Example gas chromatogram of a Soxhlet extract from a sidewall core sample from a well that was not tested until 5 years later. Predicted API=38.1° for a core extract, the measured API of DST oil overlapping the depth range of the core was 37.5°. B) Plot of Normalized Molar Percent n-Alkane vs. n-Alkane Carbon Number for SWC Extract. Predicted API=38.1°. Well was tested over 5 years later & the measured API for flowing oil was found to be 37.5°.

A gas chromatogram (GC) was analyzed from a Soxhlet extract of a sidewall core (SWC) taken from a fine grained sandstone (FIG. 6). Light hydrocarbons smaller than $nC_{15}$ were lost during the extraction. The GC peak areas are proportional to component weight percent (wt %) and are entered into the spreadsheet as raw data. FIG. 7 provides a table showing actual numbers abstracted from the spreadsheet calculator. The first step is to normalize the data so that the sum adds to 100 [Normalized wt %=(peak area*100)/sum of all areas]. The next step converts the normalized wt % to a calculated mole % using EQ. 2.

$$\text{Mole \%} = [(100 * \text{wt \% Cn/MW Cn}) / (\Sigma(\text{wt \% Cn/MW of Cn})] \quad (2)$$

The mole % are renormalized for the carbon range of interest (last column FIG. 7), in this case $nC_{17}$ to $nC_{27}$ and the result plotted on a log scale vs. the carbon number for each alkane (FIG. 6B). The resulting equation for the best linear fit line is in the form of EQ. 1 and yields the A factor (coefficient) and the B factor (exponent term). A and B are then entered into the equation derived from calibration data for the oil type that may be in the form of EQ. 3 and 4.

$$API = m \, Ln(A) + c \quad (3)$$

$$API = -xB^2 - yB + z \quad (4)$$

Terms "m, c, x, y, and z" are coefficients determined from the best fit of measured oil API vs. the calculated A or B factors for appropriate oil or condensate samples. The calculated API gravities from the A and B factors for this SWC were 38.0° and 38.1° respectively. The A (190.5855) and B (−0.1428) factors indicated this SWC contained oil and not condensate like nearby wells. This well was not tested until over 5 years later. The DST oil across this zone tested oil with API=37.5°.

Figure 12:
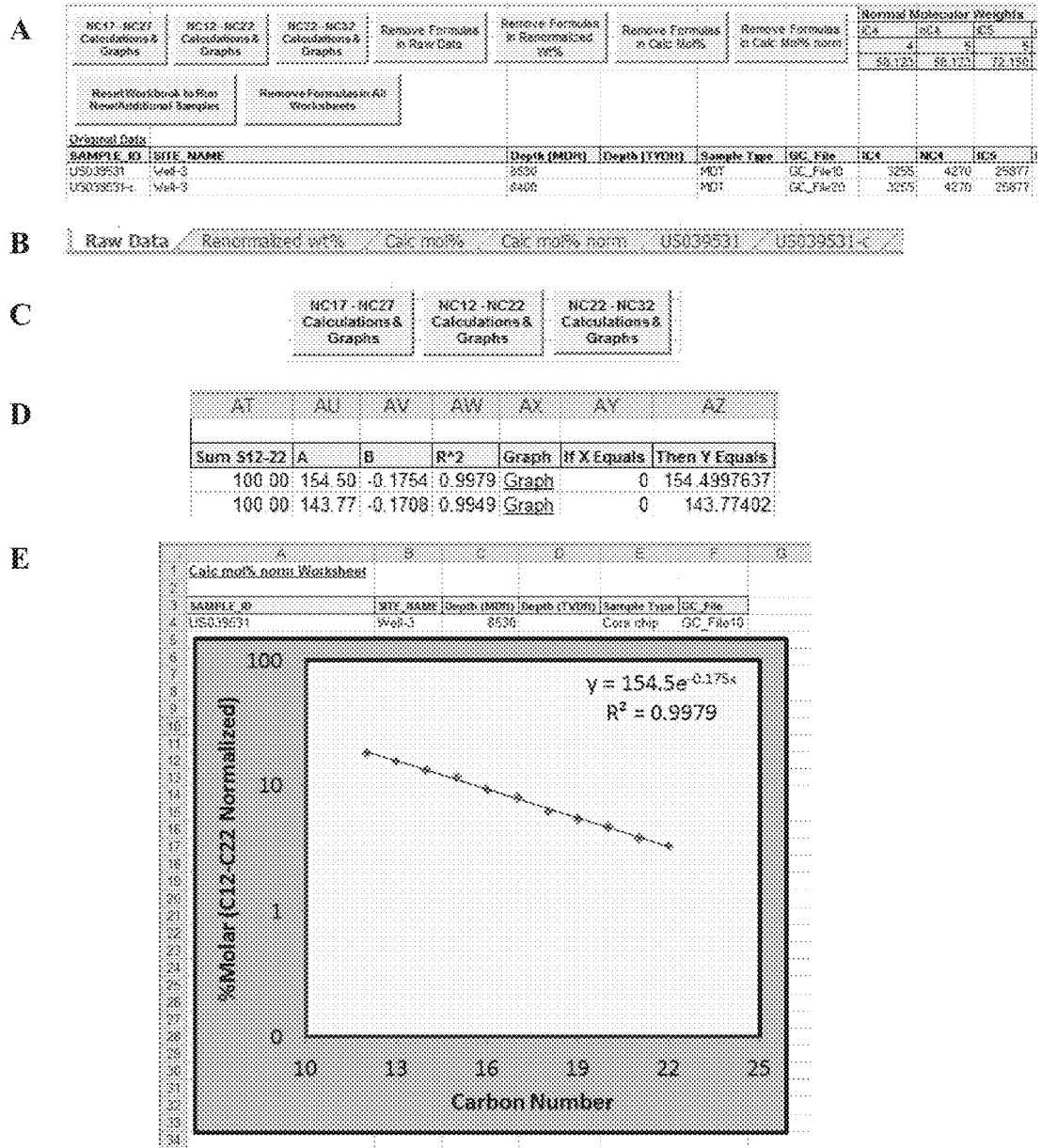
FIG. 12A-12E illustrates various steps of determining fluid property as described in the Example.

In one embodiment, the process includes the following:
  Enter the sample data on the "Raw Data" worksheet of the Mol_Calculator workbook (FIG. 12A).
  Each sample is given a unique SAMPLE_ID.
  After entry of one or more sample data on the "Raw Data" worksheet, select one of the 3 optional calculations (FIG. 12C):
  A. NC17-NC27 Calculations & Graphs
  B. NC12-NC22 Calculations & Graphs
  C. NC22-NC32 Calculations & Graphs
  The calculation will output graphs of % Molar n-Alkanes vs Carbon Number for the samples.
  Each sample will have its own worksheet created which contains its graph (FIG. 12E).
  Graphs Data is accessed in the "Calc mol % norm" worksheet (FIG. 12B).
  Each sample graph worksheet cross-references the "Calc mol % norm" worksheet allowing quick transition from samples to graphs and graphs to samples (FIG. 12D).
  Optionally, hypothetical values of X may be entered to determine the Y value in the "Calc mol % norm" worksheet.

Formulas located in the worksheets where calculations were done may be maintained or removed from the worksheets. Buttons have been provided on the "Raw Data" worksheet to remove formulas on a particular worksheet or all of the worksheets.

Figure 8:
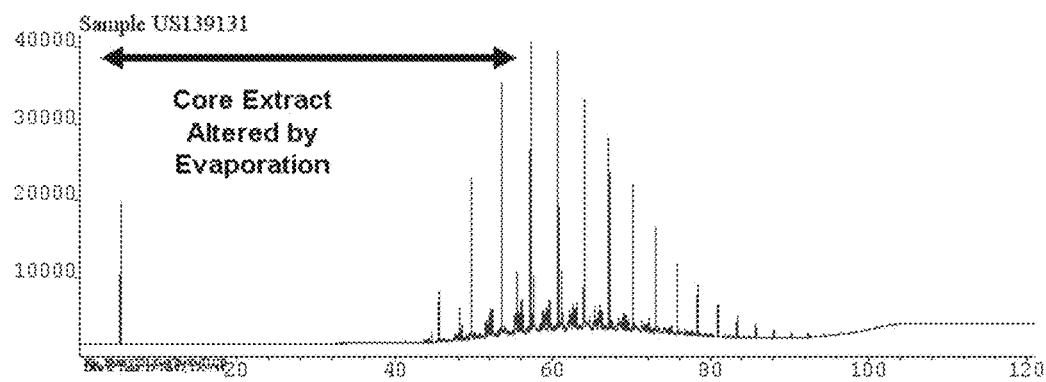
FIG. 8: Middle East Sandstone Core Extract; Altered by Evaporation.
Figure 9:
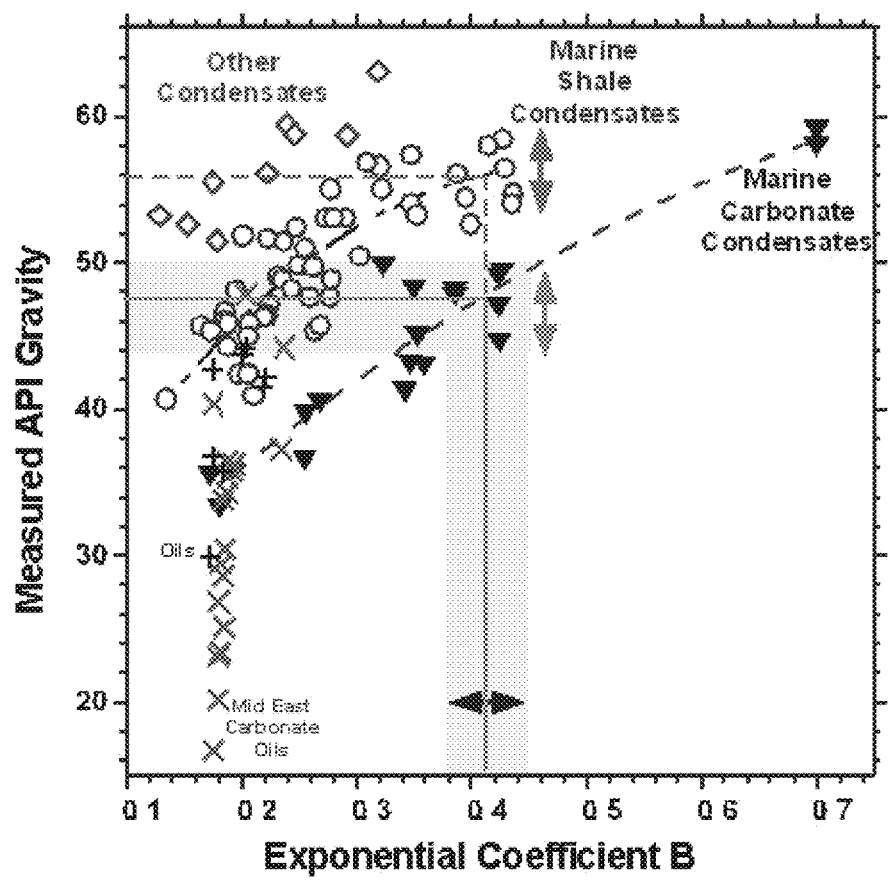
FIG. 9: Global Calibration Curve for Gas Condensates.

In order to run new or additional samples, simply press the reset button provided on the "Raw Data" worksheet. When it is pressed, it will delete all data on all the worksheets with the exception of the "Raw Data" worksheet. It will also remove all worksheets with the exception of the original four:
  Raw Data
  Renormalized wt %
  Calc mol %
  Calc mol % norm Application to Highly Evaporated Samples In one embodiment, sandstone core chips from an international well were analyzed by GC analysis (FIGS. 8 and 9). The core had been stored in less than optimal conditions for years and had experienced evaporation of all alkanes below $nC_{14}$, and extreme to moderate alteration for $nC_{14}$-$nC_{17}$ (FIG. 8). These samples were extensively altered, but application of the method provided A and B factors that indicated a gas condensate. Local oils were available for a calibration curve but no local condensates were available for analysis. Global calibration curves (FIG. 9) based upon condensates from North America, Europe, and the Middle East were generated for condensates from carbonate sources (higher sulfur, lower API gravity), marine shale derived condensates (low sulfur, higher API gravity) and condensates with exceptional high API. Other information indicated that the local source was most likely a carbonate, thus, the carbonate curve was used for prediction of API gravity. The predicted API was within one degree of an old PVT report for a test from the well. Present day workers did not trust the integrity of the original data, however, this method was able to confirm the phase as gas plus condensate and the API gravity of the condensate.

Figure 10:
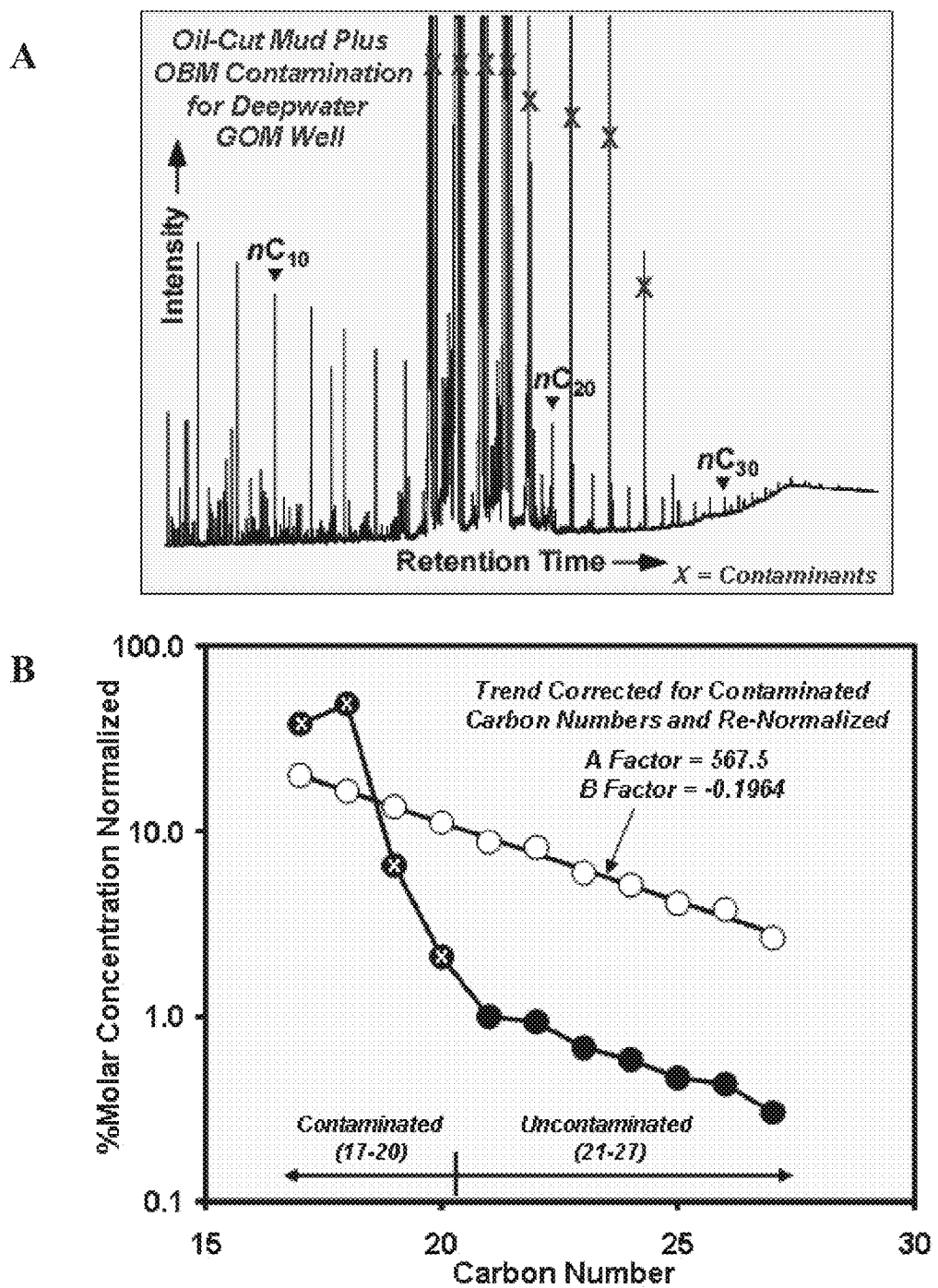
FIG. 10: Application to a contaminated sample. A) Example whole oil gas chromatogram of oil sample contaminated by oil-based drilling mud. B) Plot of uncorrected and corrected normalized percent molar n-alkane concentration on a log scale versus n-alkane carbon number.

The method also works for samples contaminated by drilling fluid materials (FIG. 10). The method can be applied to contaminated rock extracts as well as contaminated oil. The contaminants may preclude accurate direct measurement of some petroleum properties like API gravity.

Application to Contaminated Oils

Many exploration and development wells, worldwide, must be drilled with oil-based muds (OBM), often with hydrocarbon-rich additives or base oils. Fortunately, the drilling fluids and additives usually have a limited carbon range. FIG. 10A shows a light oil from the Gulf of Mexico that has been contaminated by OBM and mud additives where the n-alkanes from $nC_{15}$-$nC_{20}$ and the pseudocomponents from $nC_{15}$-$nC_{27}$ are affected. The contaminants preclude direct measurement of a contamination-free API gravity. A best fit trend was calculated for the uncontaminated n-alkanes, $nC_{21}$-$nC_{27}$. Then, the n-alkane molar per cents were calculated for $nC_{17}$-$nC_{20}$. The corrected $nC_{17}$-$nC_{27}$ trend and best fit equation, plus A and B factors is in FIG. 10B. The API gravity can be calculated from the A and B factors.

Application to Mixed Fluids

Fluids will be encountered that are mixtures of two different petroleum charges. If the mixtures are both black oils or both condensates then the normal application will generally provide a reasonable estimate of the combined producible fluid.

Figure 11A:
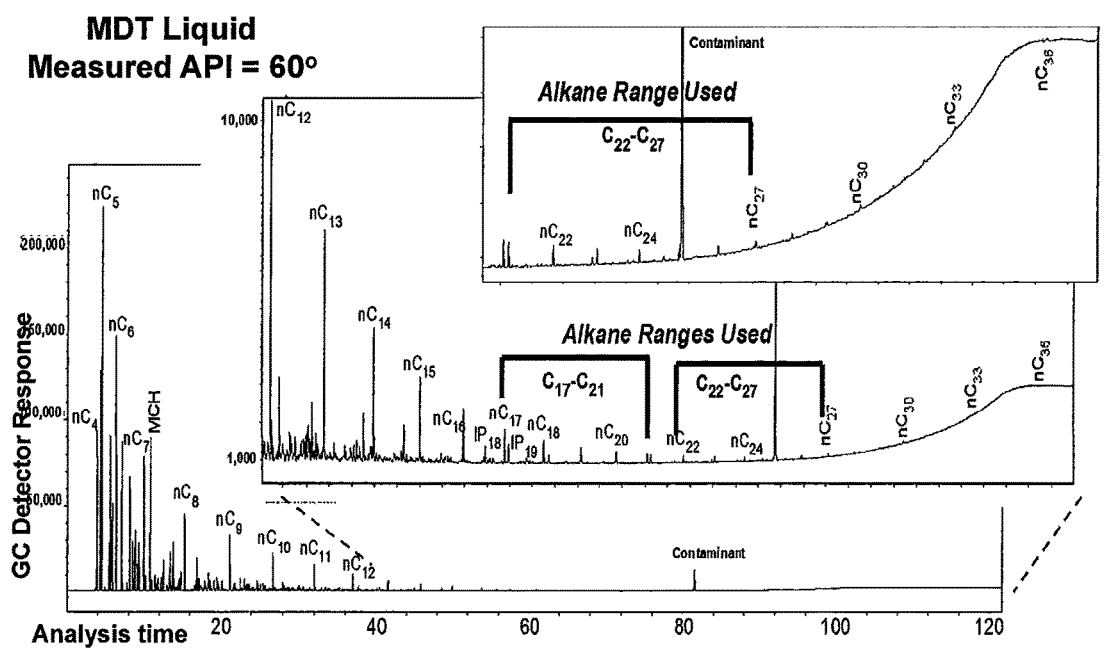
FIG. 11: Mixed Fluids with Different Slopes. This petroleum is a mixture of light condensate with small amounts of black oil present in the reservoir. The $C_7$-$C_{20}$ hydrocarbons dominate the fluid, thus the method correctly predicts (+1°) the flowing fluid API gravity when the correct range of n-alkanes is used in the method. A) gas chromatogram of API 60 condensate, b) molar slopes plot with carbon number for mixed fluid shows two slopes representing the light and heavier black oil components.
Figure 11B:
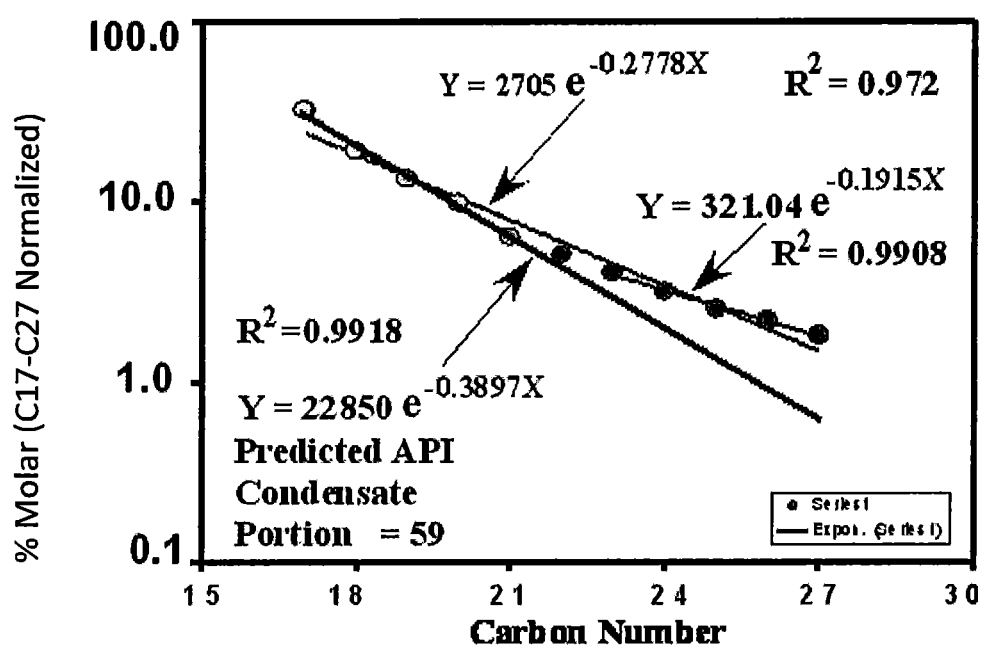

If the sample represents a mixture of a small amount of black oil with a large amount of condensate (or retrograde condensate) (FIG. 11A), then the resulting normalized molar percent n-alkanes may be able to split into two regions with two different slopes (FIG. 11B). The results for the fluid in FIG. 11 gave two different estimates; n-alkanes<$C_{21}$ predicted a gas condensate with API gravity of 59°. However, n-alkanes>$C_{21}$ predicted a black oil with a lower API gravity. The gas chromatogram shows that the major fluid constituents were <$nC_{21}$, thus a gravity of 59° was predicted. The measured API of producible fluid was 60°.

The observation of multiple slopes in the plot of normalized molar percent vs. carbon number confirms mixing of two or more distinct fluids. It also enables prediction of fluid quality for each contributing petroleum. To date, the method has been used extensively tested in oil and gas fields in the United States, the Middle East, and the former Soviet Union.

In closing, it should be noted that the discussion of any reference is not an admission that it is prior art to the present invention, especially any reference that may have a publication date after the priority date of this application. At the same time, each and every claim below is hereby incorporated into this detailed description or specification as additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

All of the references cited herein are expressly incorporated by reference. The discussion of any reference is not an admission that it is prior art to the present invention, especially any reference that may have a publication date after the priority date of this application. Incorporated references are listed again here for convenience:

REFERENCES

1. U.S. Pat. No. 5,866,814, Jones et al., "Pyrolytic Oil-Productivity Index Method for Characterizing Reservoir Rock," (1999).
2. U.S. Pat. No. 6,823,298B1, Jones, et al., "Pyrolitic Oil-Productivity Index Method for Predicting Reservoir Rock and Oil Characteristics," (2004).
3. US20070162264A1, Jones, et al., "Compositional Modeling and Pyrolysis Data Analysis Methods," (2007).
4. Baskin and Jones, (1993) Prediction of oil gravity prior to drill-stem testing in Monterey formation reservoirs, offshore California. AAPG Bulletin v, no. 9, p 1479-1487.
5. Dow and Talukdar, (1991) Petroleum geochemistry in oil production. $4^{th}$ Assn. Colombiana Geol. Geofis. Petrol. Petrol. Explor. In the Sub-Andean Basins Bolivariana Symp. Bogata, (Colombia, Mar. 10-13, 1991) Memoir v. 2, no. 51.
6. Dow, et al., "Determination of API Gravity from very small samples of oils, tar mats, and solid bitumens with Rock-Eval 6 Instrument." $18^{th}$ Annual Meeting Abstracts and Program, The Society of Organic Petrology (TSOP), p 41-42 (2001).
7. Holba, et al., "Effects and impact of early-stage anaerobic biodegradation on Kuparuk River Field, Ak." In: *Understanding Petroleum Reservoirs: Towards an Integrated Reservoir Engineering and Geochemical Approach*. (eds.: Cubitt, J. M.; England, W. A.; and Larter, S.) Geological Society, London, special Publications 237, 53-88 (2004).
8. Hughes and Holba "Relationship between crude oil quality and biomarker patterns," Advances Organic Geochemistry 1987, Organic Geochemistry, 13, nos. 1-3, 15-30 (1988).
9. Huizninga, et al., Heavy oils from the West Sak Field, North Slope Alaska: Geochemical oil property prediction and columnar gradients. (Abstract) AAPG Hedberg Conference: *Heavy Oil and Bitumen in Foreland Basins—From Process to Products*. Banff, Alberta, Canada, Sep. 30-Oct. 1 (2007).
10. Katz and Firoozabadi "Predicting phase behavior of condensate/crude-oil systems using methane interaction coefficients." SPE 6721, pp 1649-55 (1978).
11. Michael "Application of reservoir geochemistry to heavy oil, Venezuela." AAPG Annual Convention. May 11-14, (Abstract) (2003)
12. Pedersen and Christensen "Phase Behavior of Petroleum Reservoir Fluids." CRC, Taylor & Francis Group, Boca Raton, Fla., 406 p. (2007)
13. Smalley, et al., "New tools target oil quality sweetspots in viscous oil accumulations." SPE 36652 (1996).
14. Zhang, et al., Some exceptions to default NMR rock and fluid properties. $39^{th}$ Annual SPWLA Logging Symposium (Keystone Colo., 5/26-29/98) Transactions (1998).

The invention claimed is:

1. A method of analyzing a reservoir fluid property of a small volume rock extract or fluid sample, comprising:
   a) obtaining a rock extract or fluid sample from a subterranean reservoir, wherein a volume of the rock extract or fluid sample is in the microliter range;
   b) analyzing the rock extract or fluid sample by gas chromatography to provide a gas chromatogram;
   c) calculating chromatographic peak area for three or more alkanes in the gas chromatogram;
   d) selecting a representative series of three or more alkane peaks for analysis;
   e) optionally, normalizing the alkane peak areas across the representative series;
   f) optionally, converting the chromatographic peak areas of the selected series to mole percent or weight percent;
   g) obtaining a plot of the concentration in terms of peak area, mole percent or weight percent, against carbon number or molecular weight;
   h) fitting an equation to plotted concentrations obtained from (g);
   i) determining goodness of fit ($R^2$) for the equation to the plotted peaks;
   j) re-selecting the representative series of alkane peaks and repeating (e), (f), (g), (h), (i) and (j);
   k) identifying calibration petroleum sample or samples with similar plot;
   l) assigning one or more fluid properties from the calibration petroleum sample or samples to the rock extract or fluid sample with unknown property;
   m) determining the unknown property of the rock extract or fluid sample based on the assigning; and
   n) adjusting a field development operation based on the unknown property determined in step m).

2. The method of claim 1, wherein the peak area in step (g) is normalized.

3. The method of claim 1, wherein the mole percent or weight percent in step (g) is normalized.

4. The method of claim 1, wherein said selected representative series of alkanes or pseudocomponents comprises peaks or areas between $C_{10}$ and $C_{35}$.

5. The method of claim 1, wherein said representative series of alkanes or pseudocomponents comprises peaks or areas corresponding to an alkane molecular weight of approximately $C_8$-$C_{12}$, $C_{10}$-$C_{14}$, $C_{10}$-$C_{15}$, $C_{10}$-$C_{16}$, $C_{10}$-$C_{17}$, $C_{10}$-$C_{18}$, $C_{10}$-$C_{19}$, $C_{10}$-$C_{20}$, $C_{10}$-$C_{21}$, $C_{10}$-$C_{22}$, $C_{10}$-$C_{23}$, $C_{10}$-$C_{24}$, $C_{10}$-$C_{25}$, $C_{10}$-$C_{26}$, $C_{10}$-$C_{27}$, $C_{10}$-$C_{30}$, $C_{10}$-$C_{32}$, $C_{10}$-$C_{34}$, $C_{10}$-$C_{36}$, $C_{10}$-$C_{37}$, $C_{12}$-$C_{14}$, $C_{12}$-$C_{15}$, $C_{12}$-$C_{16}$, $C_{12}$-$C_{17}$, $C_{12}$-$C_{18}$, $C_{12}$-$C_{19}$, $C_{12}$-$C_{20}$, $C_{12}$-$C_{21}$, $C_{12}$-$C_{22}$, $C_{12}$-$C_{23}$, $C_{12}$-$C_{24}$, $C_{12}$-$C_{25}$, $C_{12}$-$C_{26}$, $C_{12}$-$C_{27}$, $C_{12}$-$C_{30}$, $C_{12}$-$C_{32}$, $C_{12}$-$C_{34}$, $C_{12}$-$C_{36}$, $C_{12}$-$C_{37}$, $C_{14}$-$C_{16}$, $C_{14}$-$C_{17}$, $C_{14}$-$C_{18}$, $C_{14}$-$C_{19}$, $C_{14}$-$C_{20}$, $C_{14}$-$C_{21}$, $C_{14}$-$C_{22}$, $C_{14}$-$C_{23}$, $C_{14}$-$C_{24}$, $C_{14}$-$C_{25}$, $C_{14}$-$C_{26}$, $C_{14}$-$C_{27}$, $C_{14}$-$C_{30}$, $C_{14}$-$C_{32}$, $C_{14}$-$C_{34}$, $C_{14}$-$C_{36}$, $C_{14}$-$C_{37}$ $C_{15}$-$C_{17}$, $C_{15}$-$C_{18}$, $C_{15}$-$C_{19}$, $C_{15}$-$C_{20}$, $C_{15}$-$C_{21}$, $C_{15}$-$C_{22}$, $C_{15}$-$C_{23}$, $C_{15}$-$C_{24}$, $C_{15}$-$C_{25}$, $C_{15}$-$C_{26}$, $C_{15}$-$C_{27}$, $C_{15}$-$C_{30}$, $C_{15}$-$C_{32}$, $C_{15}$-$C_{34}$, $C_{15}$-$C_{36}$, $C_{15}$-$C_{37}$, $C_{17}$-$C_{19}$, $C_{17}$-$C_{20}$, $C_{17}$-$C_{21}$, $C_{17}$-$C_{22}$, $C_{17}$-$C_{23}$, $C_{17}$-$C_{24}$, $C_{17}$-$C_{25}$, $C_{17}$-$C_{26}$, $C_{17}$-$C_{27}$, $C_{17}$-$C_{30}$, $C_{17}$-$C_{32}$, $C_{17}$-$C_{34}$, $C_{17}$-$C_{36}$, $C_{17}$-$C_{37}$, $C_{21}$-$C_{16}$, $C_{21}$-$C_{18}$, $C_{21}$-$C_{19}$, $C_{21}$-$C_{23}$, $C_{21}$-$C_{24}$, $C_{21}$-$C_{25}$, $C_{21}$-$C_{26}$, $C_{21}$-$C_{27}$, $C_{21}$-$C_{30}$, $C_{21}$-$C_{32}$, $C_{21}$-$C_{34}$, $C_{21}$-$C_{36}$, $C_{21}$-$C_{37}$, $C_{22}$-$C_{16}$, $C_{22}$-$C_{18}$, $C_{22}$-$C_{19}$, $C_{22}$-$C_{20}$, $C_{22}$-$C_{24}$, $C_{22}$-$C_{25}$, $C_{22}$-$C_{26}$, $C_{22}$-$C_{27}$, $C_{22}$-$C_{30}$, $C_{22}$-$C_{32}$, $C_{22}$-$C_{34}$, $C_{22}$-$C_{36}$, $C_{22}$-$C_{37}$, $C_{23}$-$C_{16}$, $C_{23}$-$C_{18}$, $C_{23}$-$C_{19}$, $C_{23}$-$C_{20}$, $C_{23}$-$C_{25}$, $C_{23}$-$C_{26}$, $C_{23}$-$C_{27}$, $C_{23}$-$C_{30}$, $C_{23}$-$C_{32}$, $C_{23}$-$C_{34}$, $C_{23}$-$C_{36}$, $C_{23}$-$C_{37}$, and any combination thereof.

6. The method of claim 1, wherein a chromatographic spectra is stored in a non-transitory computer medium utilizing column separated value, tab separated value, hypertext machine language, relational database, text or other format of storing chromatographic spectra.

7. A method of analyzing a reservoir fluid property of a small volume rock extract or fluid sample, comprising:
   a) obtaining a rock extract or fluid sample from a subterranean reservoir, wherein a volume of the rock extract or fluid sample is in the microliter range;
   b) analyzing the rock extract or fluid sample by gas chromatography to provide a gas chromatogram;
   c) calculating chromatographic area for three or more alkane pseudocomponents in the gas chromatogram;
   d) selecting a representative series of three or more pseudocomponent areas for analysis;
   e) optionally, normalizing the pseudocomponent peak areas across the representative series;
   f) optionally, converting the pseudocomponent peak areas of the selected series to mole percent or weight percent;
   g) obtaining a plot of the concentration in terms of pseudocomponent peak area, mole percent or weight percent against carbon number or molecular weight;
   h) fitting an equation to plotted concentrations obtained from (g);
   i) determining goodness of fit ($R^2$) for the equation to the pseudocomponent areas;
   j) re-selecting the representative series of pseudocomponent areas and repeating (e), (f), (g), (h), (i) and (j) as needed to obtain suitable goodness of fit;
   k) identifying a calibration petroleum sample with a similar plot;
   l) assigning one or more fluid properties selected from the group consisting of API gravity, fluid phase, and any combination thereof, from the calibration petroleum sample to the rock extract or fluid sample with unknown properties;
   m) determining petroleum API gravity or petroleum phase of the rock extract or fluid sample based on the assigning; and
   n) adjusting a field development operation based on the petroleum API gravity or petroleum phase of the rock extract or fluid sample determined in step m).

8. The method of claim 7, wherein the peak area in step (g) is normalized.

9. The method of claim 7, wherein the mole percent or weight percent in step (g) is normalized.

10. The method of claim 7, wherein said representative series of alkanes or pseudocomponents comprises peaks or areas between $C_{10}$ and $C_{35}$.

11. The method of claim 7, wherein said representative series of alkanes or pseudocomponents comprises peaks or areas corresponding to an alkane molecular weight of approximately $C_8$-$C_{12}$, $C_{10}$-$C_{15}$, $C_{10}$-$C_{16}$, $C_{10}$-$C_{17}$, $C_{10}$-$C_{18}$, $C_{10}$-$C_{19}$, $C_{10}$-$C_{20}$, $C_{10}$-$C_{21}$, $C_{10}$-$C_{22}$, $C_{10}$-$C_{23}$, $C_{10}$-$C_{24}$, $C_{10}$-$C_{25}$, $C_{10}$-$C_{26}$, $C_{10}$-$C_{27}$, $C_{10}$-$C_{30}$, $C_{10}$-$C_{32}$, $C_{10}$-$C_{34}$, $C_{10}$-$C_{36}$, $C_{10}$-$C_{37}$, $C_{12}$-$C_{14}$, $C_{12}$-$C_{15}$, $C_{12}$-$C_{16}$, $C_{12}$-$C_{17}$, $C_{12}$-$C_{18}$, $C_{12}$-$C_{19}$, $C_{12}$-$C_{20}$, $C_{12}$-$C_{21}$, $C_{12}$-$C_{22}$, $C_{12}$-$C_{23}$, $C_{12}$-$C_{24}$, $C_{12}$-$C_{25}$, $C_{12}$-$C_{26}$, $C_{12}$-$C_{27}$, $C_{12}$-$C_{30}$, $C_{12}$-$C_{32}$, $C_{12}$-$C_{34}$, $C_{12}$-$C_{36}$, $C_{12}$-$C_{37}$, $C_{14}$-$C_{16}$, $C_{14}$-$C_{17}$, $C_{14}$-$C_{18}$, $C_{14}$-$C_{19}$, $C_{14}$-$C_{20}$, $C_{14}$-$C_{21}$, $C_{14}$-$C_{22}$, $C_{14}$-$C_{23}$, $C_{14}$-$C_{24}$, $C_{14}$-$C_{25}$, $C_{14}$-$C_{26}$, $C_{14}$-$C_{27}$, $C_{14}$-$C_{30}$, $C_{14}$-$C_{32}$, $C_{14}$-$C_{34}$, $C_{14}$-$C_{36}$, $C_{14}$-$C_{37}$ $C_{15}$-$C_{17}$, $C_{15}$-$C_{18}$, $C_{15}$-$C_{19}$, $C_{15}$-$C_{20}$, $C_{15}$-$C_{21}$, $C_{15}$-$C_{22}$, $C_{15}$-$C_{23}$, $C_{15}$-$C_{24}$, $C_{15}$-$C_{25}$, $C_{15}$-$C_{26}$, $C_{15}$-$C_{27}$, $C_{15}$-$C_{30}$, $C_{15}$-$C_{32}$, $C_{15}$-$C_{34}$, $C_{15}$-$C_{36}$, $C_{15}$-$C_{37}$, $C_{17}$-$C_{19}$, $C_{17}$-$C_{20}$, $C_{17}$-$C_{21}$, $C_{17}$-$C_{22}$, $C_{17}$-$C_{23}$, $C_{17}$-$C_{24}$, $C_{17}$-$C_{25}$, $C_{17}$-$C_{26}$, $C_{17}$-$C_{27}$, $C_{17}$-$C_{30}$, $C_{17}$-$C_{32}$, $C_{17}$-$C_{34}$, $C_{17}$-$C_{36}$, $C_{17}$-$C_{37}$, $C_{21}$-$C_{16}$, $C_{21}$-$C_{18}$, $C_{21}$-$C_{19}$, $C_{21}$-$C_{23}$, $C_{21}$-$C_{24}$, $C_{21}$-$C_{25}$, $C_{21}$-$C_{26}$, $C_{21}$-$C_{27}$, $C_{21}$-$C_{30}$, $C_{21}$-$C_{32}$, $C_{21}$-$C_{34}$, $C_{21}$-$C_{36}$, $C_{21}$-$C_{37}$, $C_{22}$-$C_{16}$, $C_{22}$-$C_{18}$, $C_{22}$-$C_{19}$, $C_{22}$-$C_{20}$, $C_{22}$-$C_{24}$, $C_{22}$-$C_{25}$, $C_{22}$-$C_{26}$, $C_{22}$-$C_{27}$, $C_{22}$-$C_{30}$, $C_{22}$-$C_{32}$, $C_{22}$-

$C_{34}$, $C_{22}$-$C_{36}$, $C_{22}$-$C_{37}$, $C_{23}$-$C_{16}$, $C_{23}$-$C_{18}$, $C_{23}$-$C_{19}$, $C_{23}$-$C_{20}$, $C_{23}$-$C_{25}$, $C_{23}$-$C_{26}$, $C_{23}$-$C_{27}$, $C_{23}$-$C_{30}$, $C_{23}$-$C_{32}$, $C_{23}$-$C_{34}$, $C_{23}$-$C_{36}$, $C_{23}$-$C_{37}$, and any combination thereof.

12. The method of claim 7, wherein a chromatographic spectra is stored in a non-transitory computer medium utilizing column separated value, tab separated value, hypertext machine language, relational database, text or other format of storing chromatographic spectra.

13. A method of analyzing a reservoir fluid property of a contaminated, degraded, or evaporated rock extract or fluid sample, comprising:
   a) obtaining a contaminated, degraded or evaporated rock extract or fluid sample from a subterranean reservoir, wherein a volume of the contaminated, degraded or evaporated rock extract or fluid sample is in the microliter range;
   b) analyzing the contaminated, degraded or evaporated rock extract or fluid sample by gas chromatography to provide a gas chromatogram;
   c) calculating chromatographic areas for three or more alkane areas in the gas chromatogram;
   d) selecting a representative series of three or more alkane areas for analysis;
   e) optionally, normalizing the alkane peak areas across the representative series;
   f) optionally, converting the chromatographic peak areas of the selected series to mole percent or weight percent;
   g) obtaining a plot of the concentration in terms of peak area, mole percent or weight percent against carbon number or molecular weight;
   h) fitting an equation to plotted concentrations obtained from (g);
   i) determining goodness of fit ($R^2$) for the equation to the plotted peaks;
   j) re-selecting the selected series of alkane areas and repeating (e), (f), (g), (h), (i) and (j) as needed to obtain suitable goodness of fit;
   k) identifying a calibration petroleum sample with similar plot;
   l) assigning one or more fluid properties from the calibration petroleum sample to the contaminated, degraded or evaporated rock extract or fluid sample with unknown property;
   m) determining the unknown property of the rock extract or fluid sample based on the assigning; and
   n) adjusting a field development operation based on the unknown property determined in step m).

14. The method of claim 13, wherein said selected representative series of alkanes or pseudocomponents comprises peaks or areas between $C_{10}$ and $C_{35}$.

15. The method of claim 13, wherein said selected representative series of alkanes or pseudocomponents comprises peaks or areas corresponding to an alkane molecular weight of approximately $C_8$-$C_{12}$, $C_{10}$-$C_{14}$, $C_{10}$-$C_{15}$, $C_{10}$-$C_{16}$, $C_{10}$-$C_{17}$, $C_{10}$-$C_{18}$, $C_{10}$-$C_{19}$, $C_{10}$-$C_{20}$, $C_{10}$-$C_{21}$, $C_{10}$-$C_{22}$, $C_{10}$-$C_{23}$, $C_{10}$-$C_{24}$, $C_{10}$-$C_{25}$, $C_{10}$-$C_{26}$, $C_{10}$-$C_{27}$, $C_{10}$-$C_{30}$, $C_{10}$-$C_{32}$, $C_{10}$-$C_{34}$, $C_{10}$-$C_{36}$, $C_{10}$-$C_{37}$, $C_{12}$-$C_{14}$, $C_{12}$-$C_{15}$, $C_{12}$-$C_{16}$, $C_{12}$-$C_{17}$, $C_{12}$-$C_{18}$, $C_{12}$-$C_{19}$, $C_{12}$-$C_{20}$, $C_{12}$-$C_{21}$, $C_{12}$-$C_{22}$, $C_{12}$-$C_{23}$, $C_{12}$-$C_{24}$, $C_{12}$-$C_{25}$, $C_{12}$-$C_{26}$, $C_{12}$-$C_{27}$, $C_{12}$-$C_{30}$, $C_{12}$-$C_{32}$, $C_{12}$-$C_{34}$, $C_{12}$-$C_{36}$, $C_{12}$-$C_{37}$, $C_{14}$-$C_{16}$, $C_{14}$-$C_{17}$, $C_{14}$-$C_{18}$, $C_{14}$-$C_{19}$, $C_{14}$-$C_{20}$, $C_{14}$-$C_{21}$, $C_{14}$-$C_{22}$, $C_{14}$-$C_{23}$, $C_{14}$-$C_{24}$, $C_{14}$-$C_{25}$, $C_{14}$-$C_{26}$, $C_{14}$-$C_{27}$, $C_{14}$-$C_{30}$, $C_{14}$-$C_{32}$, $C_{14}$-$C_{34}$, $C_{14}$-$C_{36}$, $C_{14}$-$C_{37}$, $C_{15}$-$C_{17}$, $C_{15}$-$C_{18}$, $C_{15}$-$C_{19}$, $C_{15}$-$C_{20}$, $C_{15}$-$C_{21}$, $C_{15}$-$C_{22}$, $C_{15}$-$C_{23}$, $C_{15}$-$C_{24}$, $C_{15}$-$C_{25}$, $C_{15}$-$C_{26}$, $C_{15}$-$C_{27}$, $C_{15}$-$C_{30}$, $C_{15}$-$C_{32}$, $C_{15}$-$C_{34}$, $C_{15}$-$C_{36}$, $C_{15}$-$C_{37}$, $C_{17}$-$C_{19}$, $C_{17}$-$C_{20}$, $C_{17}$-$C_{21}$, $C_{17}$-$C_{22}$, $C_{17}$-$C_{23}$, $C_{17}$-$C_{24}$, $C_{17}$-$C_{25}$, $C_{17}$-$C_{26}$, $C_{17}$-$C_{27}$, $C_{17}$-$C_{30}$, $C_{17}$-$C_{32}$, $C_{17}$-$C_{34}$, $C_{17}$-$C_{36}$, $C_{17}$-$C_{37}$, $C_{21}$-$C_{16}$, $C_{21}$-$C_{18}$, $C_{21}$-$C_{19}$, $C_{21}$-$C_{23}$, $C_{21}$-$C_{24}$, $C_{21}$-$C_{25}$, $C_{21}$-$C_{26}$, $C_{21}$-$C_{27}$, $C_{21}$-$C_{30}$, $C_{21}$-$C_{32}$, $C_{21}$-$C_{34}$, $C_{21}$-$C_{36}$, $C_{21}$-$C_{37}$, $C_{22}$-$C_{16}$, $C_{22}$-$C_{18}$, $C_{22}$-$C_{19}$, $C_{22}$-$C_{20}$, $C_{22}$-$C_{24}$, $C_{22}$-$C_{25}$, $C_{22}$-$C_{26}$, $C_{22}$-$C_{27}$, $C_{22}$-$C_{30}$, $C_{22}$-$C_{32}$, $C_{22}$-$C_{34}$, $C_{22}$-$C_{36}$, $C_{22}$-$C_{37}$, $C_{23}$-$C_{16}$, $C_{23}$-$C_{18}$, $C_{23}$-$C_{19}$, $C_{23}$-$C_{20}$, $C_{23}$-$C_{25}$, $C_{23}$-$C_{26}$, $C_{23}$-$C_{27}$, $C_{23}$-$C_{30}$, $C_{23}$-$C_{32}$, $C_{23}$-$C_{34}$, $C_{23}$-$C_{36}$, $C_{23}$-$C_{37}$, and any combination thereof.

16. The method of claim 13, wherein a chromatographic spectra is stored in a non-transitory computer medium utilizing column separated value, tab separated value, hypertext machine language, relational database, text or other format of storing chromatographic spectra.

* * * * *